United States Patent
Zheng et al.

(10) Patent No.: US 7,173,046 B2
(45) Date of Patent: Feb. 6, 2007

(54) CD40:CD154 BINDING INTERRUPTER COMPOUNDS AND USE THEREOF TO TREAT IMMUNOLOGICAL COMPLICATIONS

(75) Inventors: Zhongli Zheng, Lexington, MA (US); Mary-Beth Carter, Arlington, MA (US); YuSheng Liao, Lexington, MA (US); Lihong Sun, Arlington, MA (US); Leonid Kirkovsky, San Diego, CA (US); Susan Mrose, Brookline, MA (US); Yen-Ming Hsu, Lexington, MA (US); David Thomas, Houston, TX (US); Gerald W. Shipps, Jr., Stoneham, MA (US); Satish Jindal, Milton, MA (US); George R. Lenz, Andover, MA (US); Huw M. Nash, Cambridge, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 10/377,928

(22) Filed: Feb. 28, 2003

(65) Prior Publication Data
US 2004/0067982 A1    Apr. 8, 2004

Related U.S. Application Data

(63) Continuation of application No. PCT/US01/27361, filed on Aug. 31, 2001.
(60) Provisional application No. 60/230,055, filed on Sep. 1, 2000.

(51) Int. Cl.
*A61K 31/4439* (2006.01)
*C07D 401/14* (2006.01)

(52) U.S. Cl. .............. 514/333; 514/332; 546/255; 546/256; 546/257

(58) Field of Classification Search ........... 546/255, 546/256, 257; 514/332, 333, 334
See application file for complete search history.

(56) References Cited

U.S. PATENT DOCUMENTS 5,354,761 A * 10/1994 Stanek et al. ............. 514/334
5,474,771 A   12/1995 Lederman et al.

FOREIGN PATENT DOCUMENTS

| EP | 0 541 042 | 5/1993 |
| WO | WO 99/35109 | 7/1999 |
| WO | WO 00/22649 | 4/2000 |

OTHER PUBLICATIONS

Pryor et al., "The Activated Core Approach to Combinatorial Chemistry: A Selection of New Core Molecules" Tetrahedron 54: 4107-4124 (1998).

* cited by examiner

*Primary Examiner*—Patricia L. Morris
(74) *Attorney, Agent, or Firm*—Fish & Neave IP Group of Ropes & Gray LLP; James F. Haley, Jr.; Margaret A. Pierri

(57) ABSTRACT

The present invention relates to novel CD40:CD154 binding interrupter compounds and use of these compounds and pharmaceutical compositions comprising them, to treat conditions associated with inappropriate CD154 activation in a subject. Specifically, this invention provides compounds which are identified by screening a library of small molecules for those that are capable of specifically binding CD154 and interrupting CD40:CD154 interaction.

6 Claims, No Drawings

CD40:CD154 BINDING INTERRUPTER COMPOUNDS AND USE THEREOF TO TREAT IMMUNOLOGICAL COMPLICATIONS

CROSS-REFERENCE TO RELATED APPLICATION

This application is a continuation of PCT application No. PCT/US01/27361, filed Aug. 31, 2001, which claims benefit of U.S. provisional application No. 60/230,055, filed Sep. 1, 2000. The disclosures of PCT application No. PCT/US01/27361 and U.S. provisional application No. 60/230,055 are hereby incorporated by reference herein.

TECHNICAL FIELD OF THE INVENTION

The present invention relates to novel CD40:CD154 binding interrupter compounds and use of these compounds and pharmaceutical compositions comprising them, to treat conditions associated with inappropriate CD154 activation in a subject. Specifically, this invention provides compounds which are identified by screening a library of small molecules for those that are capable of specifically binding CD154 and interrupting CD40:CD154 interaction.

BACKGROUND OF THE INVENTION

Data establishing that T cell activation requires both T cell receptor ("TCR") mediated signals and simultaneously delivered costimulatory signals have accumulated over the past twenty years. For example, antibody production by B lymphocytes in response to protein antigens requires a specific, costimulatory interaction with T lymphocytes. This B cell/T cell interaction is mediated through several receptor-ligand binding events in addition to engagement of the TCR. See, e.g., Noelle et al. *Immunology Today* 13: 431–433 (1992). See also Hollenbaugh et al. *EMBO J.* 11: 4313–4321 (1992). These additional binding events include the binding of CD40 on B cells to CD154 (CD40L, and also known as gp39, T-BAM, 5c8 antigen, CD40CR and TRAP) on T cells. Human CD40 is a 50 kilodalton cell surface protein expressed on mature B cells, as well as macrophages, dendritic cells, fibroblasts and activated endothelial cells. CD40 belongs to a class of receptors involved in cell signalling and in programmed cell death, including Fas/CD95 and the tumor necrosis factor (TNF) alpha receptor. Human CD154, a 32 kD type II membrane glycoprotein having homology to TNF alpha, is a member of the TNF family of receptors and is transiently expressed primarily on activated T cells. CD40:CD154 binding has been shown to be required for T cell-dependent antibody responses. In particular, CD40:CD154 binding provides anti-apoptotic and/or lymphokine stimulatory signals. See, e.g., Karpusas et al. *Structure* 15, 1021–1039 (1995), U.S. patent application Ser. No. 09/180,209 and WO97/00895, the disclosures of all of which are hereby incorporated by reference.

The importance of CD40:CD154 binding in promoting T cell dependent biological responses is underscored by the development of X-linked hyper-IgM syndrome (X-HIGM) in humans lacking functional CD154. These individuals have normal or high IgM levels, but fail to produce IgG, IgA or IgE antibodies. Affected individuals suffer from recurrent, sometimes severe, bacterial infection (most commonly *Streptococcus pneumoniae*, *Pneumocystis carinii* and *Hemophilus influenzae*) and certain unusual parasitic infections, as well as an increased incidence of lymphomas and abdominal cancers. These clinical manifestations of disease can be managed through intravenous immunoglobulin replacement therapy.

The effects of X-HIGM are simulated in animals rendered nullizygous for the gene encoding CD154 (knockout animals). Studies with nullizygotes have confirmed that, while B cells can produce IgM in the absence of CD40:CD154 binding, they are unable to undergo isotype switching, or to survive normally and undergo affinity maturation. In the absence of a functional CD40:CD154 interaction, spleen and lymph node germinal centers do not develop properly, and the development of memory B cells is impaired. These defects contribute to a severe reduction or absence of a secondary (mature) antibody response.

Individuals with X-HIGM and CD154 nullizygotes also have defects in cellular immunity. These defects are manifested by an increased incidence of *Pneumocystis carinii*, *Histoplasma capsulatum*, *Cryptococcus neoformans* infection, as well as chronic *Giardia lambli* infection. Murine nullizygotes are deficient in their ability to fight *Leishmania* infection. Many of these cell-mediated defects are reversible by administration of IL-12 or IFN-gamma. These data substantiate the view that CD40:CD154 binding promotes the development of Type I T-helper cell responses. Further support is derived from the observation that macrophage activation is defective in CD154-deficient settings, and that administration of anti-CD154 antibodies to mice diminished their ability to clear *Pneumocystis* infection. Blockade of CD40:CD154 binding appears to reduce the ability of macrophages to produce nitric oxide, which mediates many of the macrophages' pro-inflammatory activities. It should be noted, however, that mammals (including humans) who lack functional CD154 do not develop significant incidences of viral infection.

A number of preclinical studies, including those described in co-pending, commonly assigned PCT patent applications published as WO98/30241, WO98/30240, WO98/52606, WO98/58669 and WO99/45958, describe the promise of agents capable of interrupting CD40:CD154 binding as immunomodulating agents. In murine systems, antibodies to CD154 block primary and secondary immune responses to exogenous antigens, both in vitro and in vivo. Antibodies to CD154 cause a reduction in germinal centers in mice and monkeys, consistent with data on CD154 immunodeficiency. Administration of three doses of anti-CD154 antibody to lupus-prone mice, age three months, substantially reduced titers against double-stranded DNA and nucleosomes, delayed the development of severe nephritis, and reduced mortality. Moreover, administration of anti-CD154 antibodies to mice age five to seven months with severe nephritis was shown to stabilize or even reverse renal disease. Anti-CD154 antibodies given concomitantly with small resting allogeneic lymphocytes permitted unlimited survival of mouse pancreatic islet allografts. In other animal models, interference with CD40:CD154 binding has been demonstrated to reduce symptoms of autoimmune disease (e.g., multiple sclerosis, rheumatoid arthritis, inflammatory bowel disease), graft rejection (e.g., cardiac allograft, graft-versus-host disease), and mercuric chloride induced glomerulonephritis, which is mediated by both humoral and cellular mechanisms.

Such studies with anti-CD154 antibodies demonstrate the role of CD154 as a critical target for modulating immune responses.

These studies establish the utility of CD40:CD154 binding interrupters as therapeutic agents. As a result, they also suggest the potential of novel CD40:CD154 binding interrupters.

SUMMARY OF THE INVENTION

The present invention provides novel compounds, other than anti-CD154 antibodies and soluble CD40 or CD40 fusion proteins, that specifically bind CD154 and interrupt CD40:CD154 interaction. This invention also provides pharmaceutical compositions comprising these compounds. The invention also provides methods using these compounds to treat conditions associated with inappropriate CD154 activation.

The foregoing and other objects, features and advantages of the present invention, as well as the invention itself, will be more fully understood from the following description of preferred embodiments.

DETAILED DESCRIPTION OF THE INVENTION

The following discussion illustrates and exemplifies the variety of contexts and circumstances in which the invention can be practiced, as well as providing specific embodiments of the invention.

Novel CD40:CD154 Binding Interruptors

In a preferred embodiment, this invention provides a generic compound, which binds to CD154 and preferably interrupts CD40:CD154 interaction, represented by the formula (Formula I):

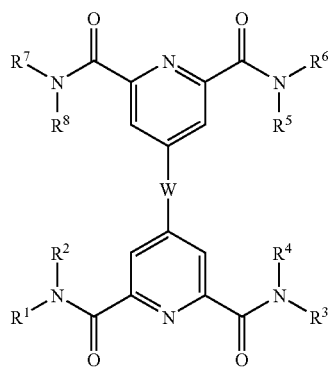

wherein:
$R^1$, $R^2$, $R^3$, $R^4$, $R^5$, $R^6$, $R^7$ and $R^8$ are independently selected from the group consisting of H, C1–5 alkyl, C1–5 alkyl-aryl, C1–5 alkyl-cycloalkyl, C1–5 alkyl-heteroaryl, C1–5 alkenyl-heterocyclo, cycloalkyl, cycloalkyl-aryl, C1–5 alkenyl-aryl, $CR^gR^hCO_2H$ and $CR^gR^hCO_2$alkyl; wherein aryl or heteroaryl are optionally substituted with one to four substituents selected from $R^d$ and alkyl is optionally substituted with $R^i$; or $R^1$ and $R^2$, $R^3$ and $R^4$, $R^5$ and $R^6$, and $R^7$ and $R^8$ independently form, together with the nitrogen to which they are attached, a 5–6 membered ring which is optionally substituted with a heteroatom selected from the group consisting of nitrogen, sulfur and oxygen, wherein the nitrogen may optionally be substituted with alkyl or alkyl-aryl and the ring may optionally be substituted with $R^j$;

$R^a$, $R^b$ and $R^c$ are independently selected from the group consisting of H, alkyl and alkyl-aryl;

$R^d$ is selected from the group consisting of halogen, alkyloxy, $NO_2$, $NH_2$, alkyl, $SO_2NH_2$, hydroxyl and aryl;

$R^e$ and $R^f$ are independently selected from the group consisting of H, alkyl and cycloalkyl; or $R^eR^f$ together with the atom to which they are attached form a 4–7 membered ring containing zero to three heteroatoms selected from the group consisting of nitrogen, oxygen and sulfur, wherein $R^eR^f$ together with the atom to which they are attached may be fused to one or two aromatic rings;

$R^g$ and $R^h$ are independently selected from the group consisting of H, alkyl, aryl, cycloalkyl, alkyl-aryl and alkyl-cycloalkyl; wherein alkyl is optionally substituted with $R^k$; and aryl is optionally substituted with $R^l$; or $R^gR^h$ together with the carbon to which they are attached form a 5–8 membered ring which may be bicyclic;

$R^i$ is selected from the group consisting of: $NR^eR^f$, alkyloxy, aryloxy, C(O)aryl, aryl, OC(O)alkyl, alkylaryloxy and hydroxyl; wherein alkyl is optionally substituted with halogen and aryl is optionally substituted with $R^d$;

$R^j$ is selected from the group consisting of $(CH_2)_yNR^eR^f$, $(CH_2)_zOH$, $CO_2H$, $C(O)N(alkyl)_2$, $C(O)NH_2$, alkylaryl and aryl;

wherein aryl is optionally substituted with one to four substituents selected from $R^d$;

$R^k$ is selected from the group consisting of $C(O)NH_2$, C(O)OH, alkylthio, $NH_2$, heteroaryl, heteroalkyl, NHC(NH)$NH_2$, C1–5 alkylhydroxyl, hydroxyl and alkyloxy;

$R^l$ is selected from the group consisting of hydroxyl, $NO_2$ and C1–5 alkyl;

U is selected from the group consisting of O, $S(O)_y$, $NR^c$, $NR^cC(O)$, $NR^cC(O)NR^c$;

W is selected from the group consisting of $(CR^aR^b)_x$, $(CR^aR^b)_yU(CR^aR^b)_y$, C2–3 alkynyl, C2–3 alkenyl;

each X is independently 0–3;

each Y is independently 0–2;

each Z is independently 1–2.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentenyl, 2-heptynyl and the like.

"Cycloalkyl" means mono- or bicyclic saturated carbocyclic rings, each of which have from 3 to 10 carbon atoms. The term also includes monocyclic rings fused to an aryl group in which the point of attachment is on the non-aromatic portion. Examples of cycloalkyl include cyclopropyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes an aryl group fused to a monocyclic cycloalkyl or monocyclic heterocyclyl group in which the point of attachment is on the aromatic portion. Examples of an aryl group include phenyl, naphthyl, indanyl, indenyl, tetrahydronaphthyl, 2,3 dihydrobenzofuranyl, benzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b) pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4 pyridones attached through the nitrogen or N-substituted-(1H,3H) pyrimidine-2,4-diones (N-substituted uracils).

"Halogen" includes fluorine, chlorine, bromine and iodine.

In a more preferred embodiment, this invention provides a compound that is a subgenera of the compound of Formula (I), said compound, which binds to CD154 and preferably interrupts CD40:CD154 interaction, being represented by the formula (Formula II):

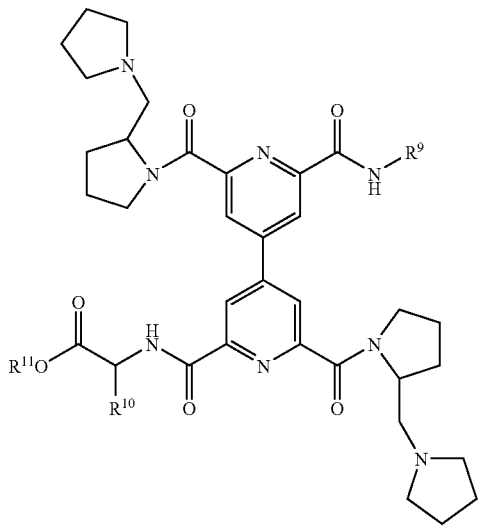

wherein:
$R^9$ is selected from the group consisting of C1–5 alkyl-aryl, cycloalkyl and alkenylaryl; wherein the alkyl is optionally substituted with aryl and the aryl is optionally substituted with one to four halogens, aryl, $NH_2$ or $NO_2$;
$R^{10}$ is selected from the group consisting of alkyl and cycloalkyl; and
$R^{11}$ is selected from the group consisting of H and alkyl.

In another more preferred embodiment, this invention provides a compound that is another subgenera of the compound of Formula (I) and is a subgenera of the compound of Formula (II), said compound, which binds to CD154 and preferably interrupts CD40:CD154 interaction, being represented by the formula (Formula III):

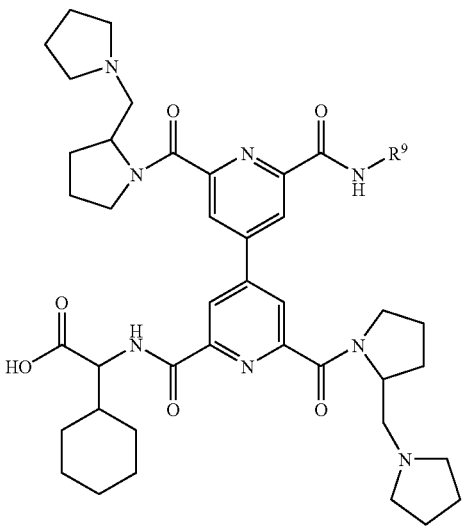

wherein:
$R^9$ is selected from the group consisting of C1–5 alkyl-aryl; wherein alkyl and aryl are optionally substituted with aryl.

This invention also provides all stereoisomers, including enantiomers, of each of the compounds above. In a preferred embodiment, the compounds are derived from S-amines (L amino acids).

The most preferred embodiments of this invention are the twenty-one compounds shown below. All twenty-one compounds are compounds according to Formula (I). All twenty-one compounds are derived from S-amines. Seventeen of the twenty-one compounds are also compounds according to Formula (II); and five of these seventeen compounds are also compounds according to Formula (III).

Compound 1, which interrupts CD40:CD154 interaction, is a compound according to Formula (II); compound 1 being represented by the formula:

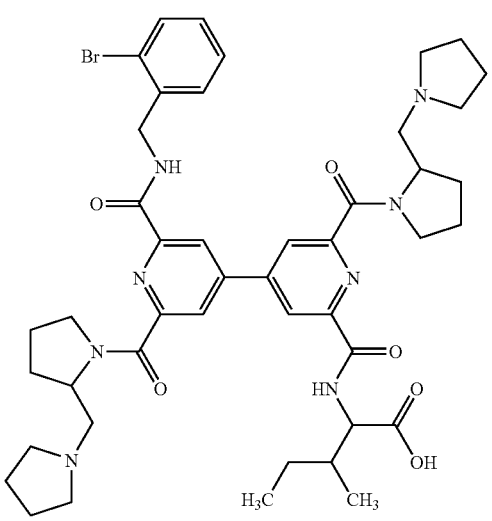

wherein: compound 1 is derived from S-amines.

Compound 2, which interrupts CD40:CD154 interaction, is a compound according to Formula (I); compound 2 being represented by the formula:

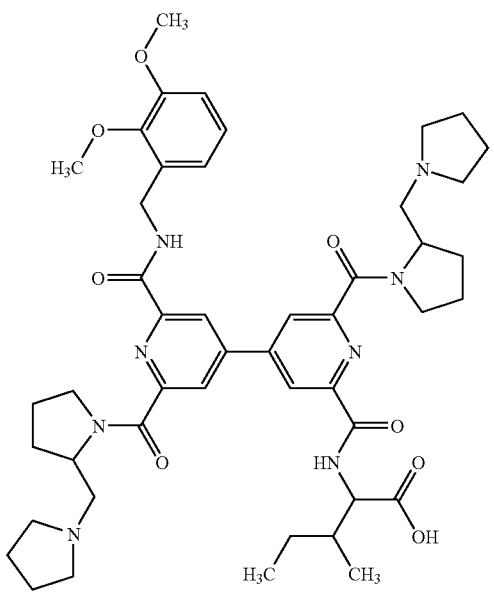

wherein: compound 2 is derived from S-amines.

Compound 3, which interrupts CD40:CD154 interaction, is a compound according to Formula (II); compound 3 being represented by the formula:

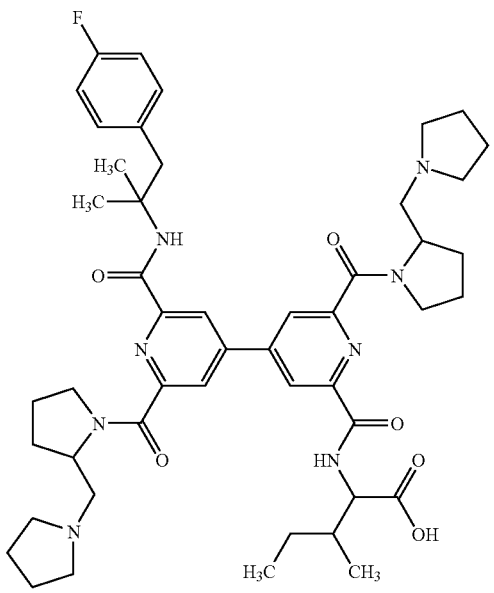

wherein: compound 3 is derived from S-amines.

Compound 4, which interrupts CD40:CD154 interaction, is a compound according to Formula (III); compound 4 being represented by the formula:

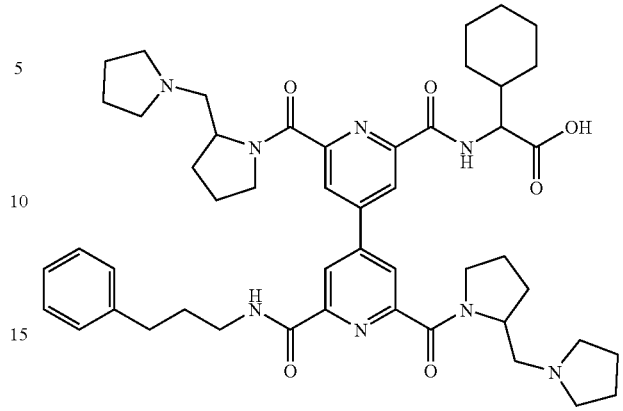

wherein: compound 4 is derived from S-amines.

Compound 5, which interrupts CD40:CD154 interaction, is a compound according to Formula (III); compound 5 being represented by the formula:

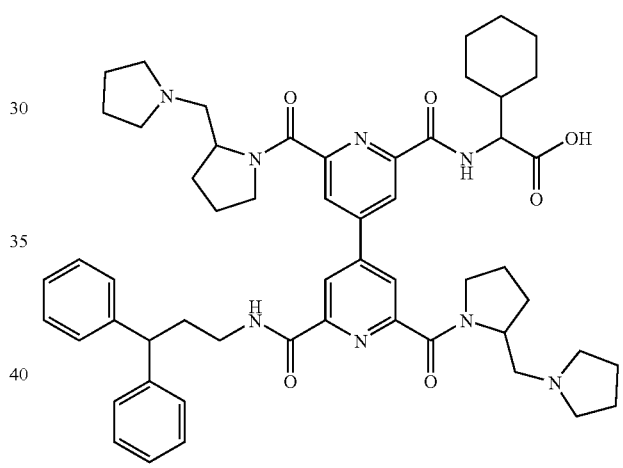

wherein: compound 5 is derived from S-amines.

Compound 6, which interrupts CD40:CD154 interaction, is a compound according to Formula (III); compound 6 being represented by the formula:

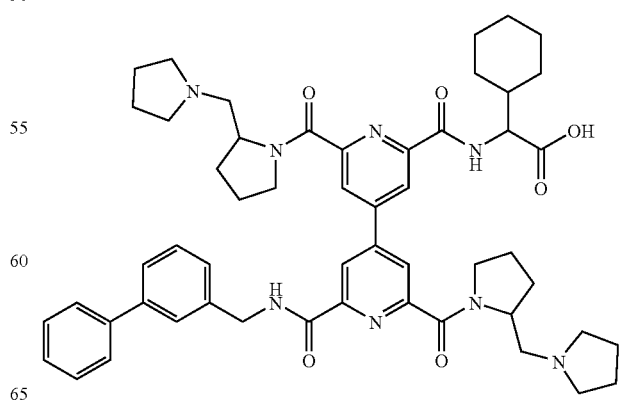

wherein: compound 6 is derived from S-amines.

Compound 7, which interrupts CD40:CD154 interaction, is a compound according to Formula (II); compound 7 being represented by the formula:

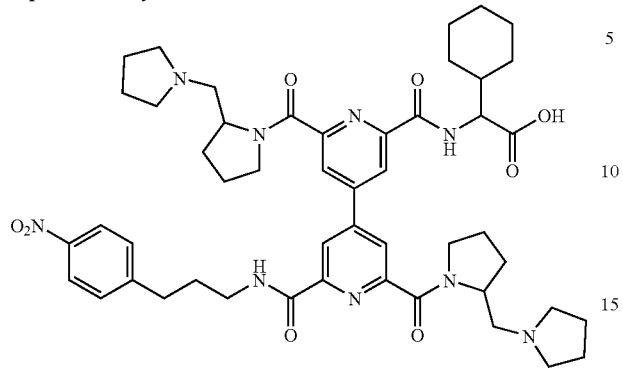

wherein: compound 7 is derived from S-amines.

Compound 8, which interrupts CD40:CD154 interaction, is a compound according to Formula (II); compound 8 being represented by the formula:

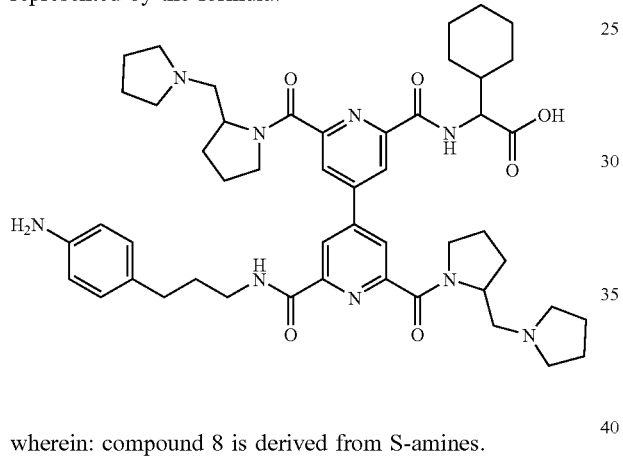

wherein: compound 8 is derived from S-amines.

Compound 9, which interrupts CD40:CD154 interaction, is a compound according to Formula (II);

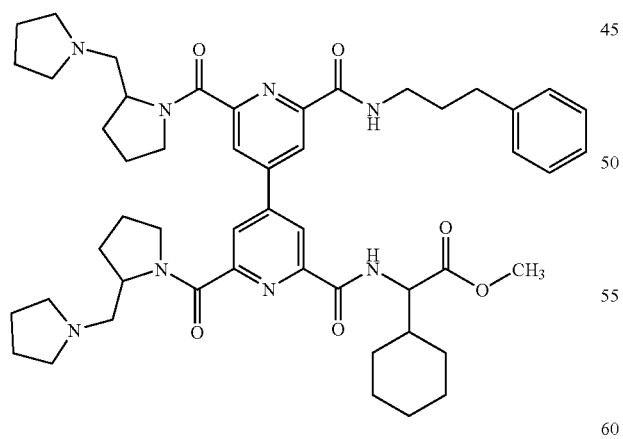

compound 9 being represented by the formula: wherein: compound 9 is derived from S-amines.

Compound 10, which interrupts CD40:CD154 interaction, is a compound according to Formula (II); compound 10 being represented by the formula:

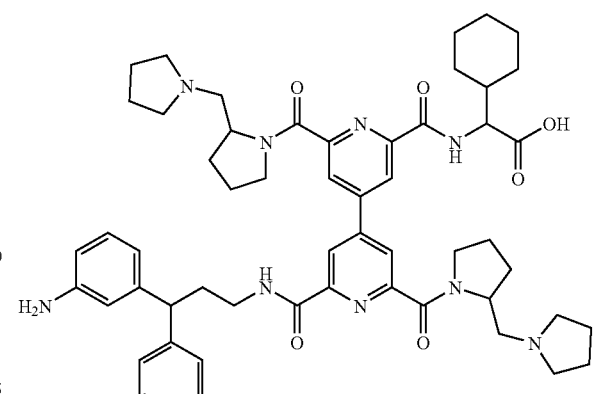

wherein: compound 10 is derived from S-amines.

Compound 11, which interrupts CD40:CD154 interaction, is a compound according to Formula (II), compound 11 being represented by the formula:

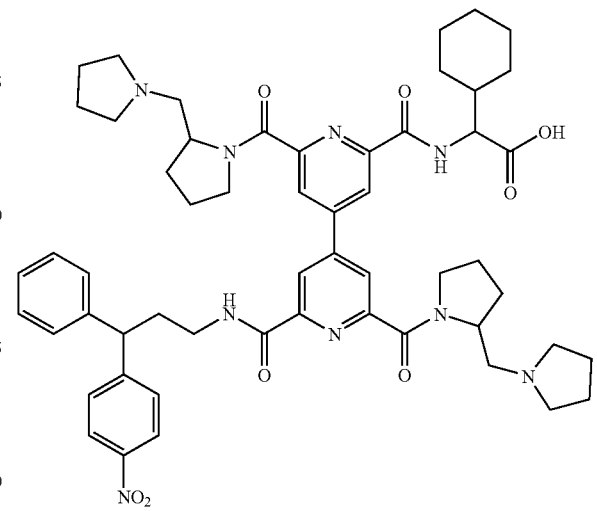

wherein: compound 11 is derived from S-amines.

Compound 12, which interrupts CD40:CD154 interaction, is a compound according to Formula (II); compound 12 being represented by the formula:

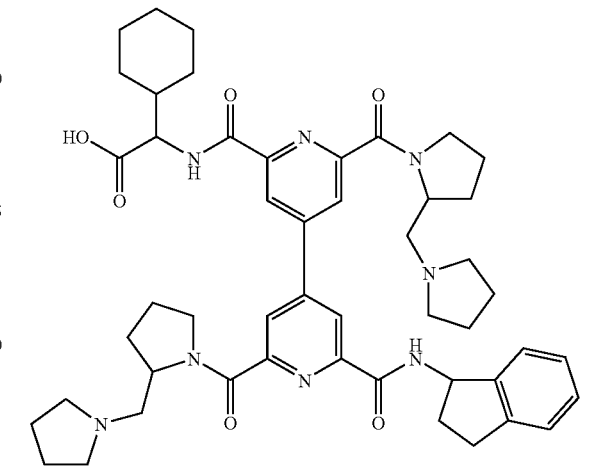

wherein: compound 12 is derived from S-amines.

Compound 13, which interrupts CD40:CD154 interaction, is a compound according to Formula (III); compound 13 being represented by the formula:

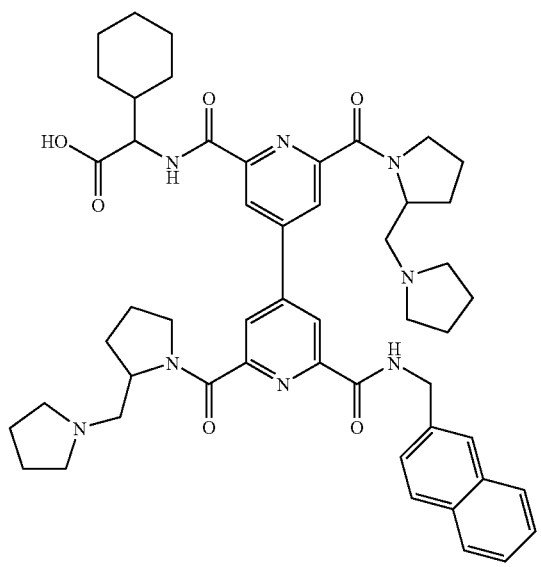

wherein: compound 13 is derived from S-amines.

Compound 14, which interrupts CD40:CD154 interaction, is a compound according to Formula (II), compound 14 being represented by the formula:

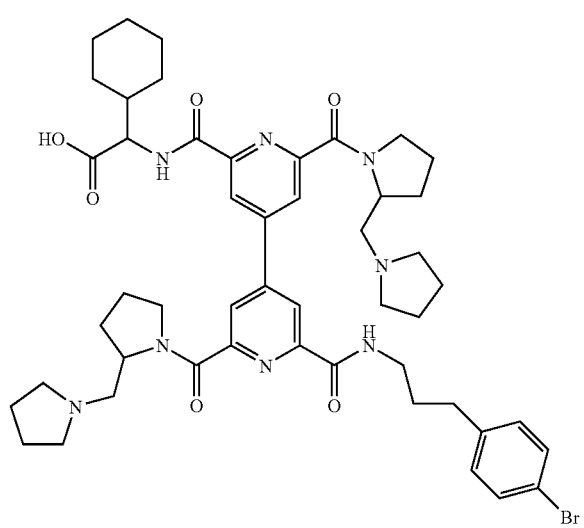

wherein: compound 14 is derived from S-amines.

Compound 15, which interrupts CD40:CD154 interaction, is a compound according to Formula (III); compound 15 being represented by the formula:

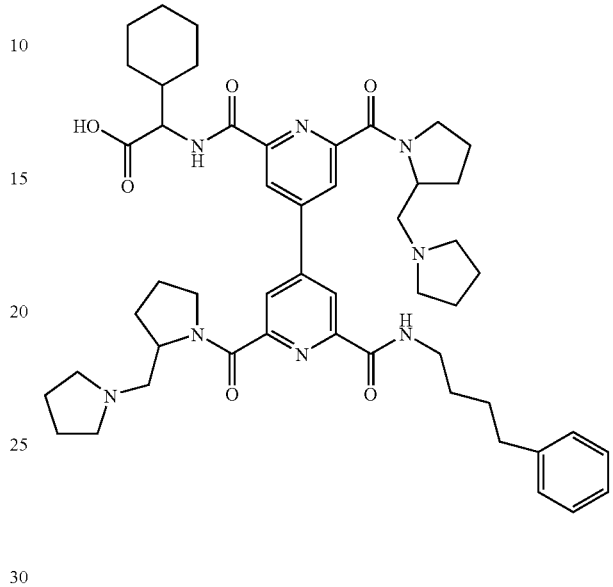

wherein: compound 15 is derived from S-amines.

Compound 16, which interrupts CD40:CD154 interaction, is a compound according to Formula (II), compound 16 being represented by the formula:

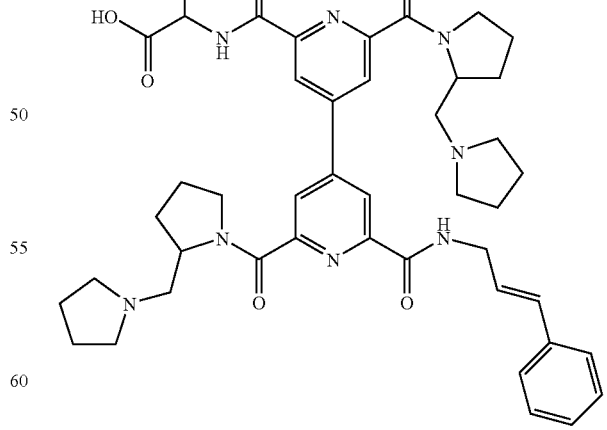

wherein: compound 16 is derived from S-amines.

Compound 17, which interrupts CD40:CD154 interaction, is a compound according to Formula (I), compound 17 being represented by the formula:

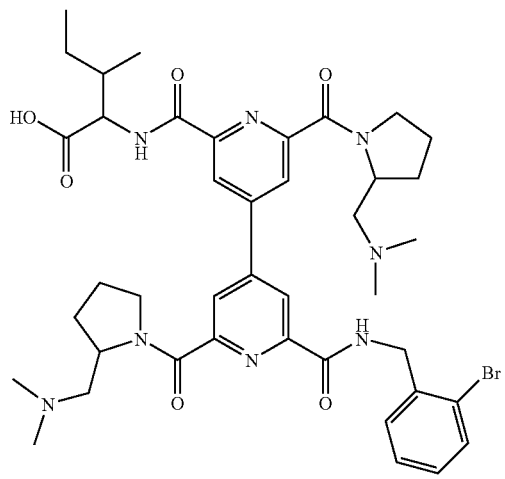

wherein: compound 17 is derived from S-amines.

Compound 18, which interrupts CD40:CD154 interaction, is a compound according to Formula (I), compound 18 being represented by the formula:

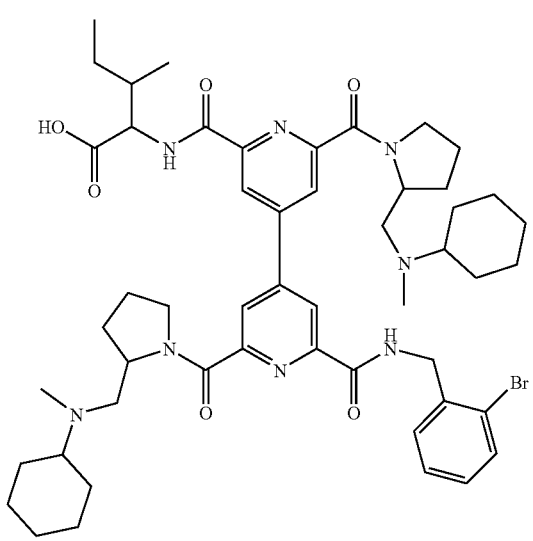

wherein: compound 18 is derived from S-amines.

Compound 19, which interrupts CD40:CD154 interaction, is a compound according to Formula (I), compound 19 being represented by the formula:

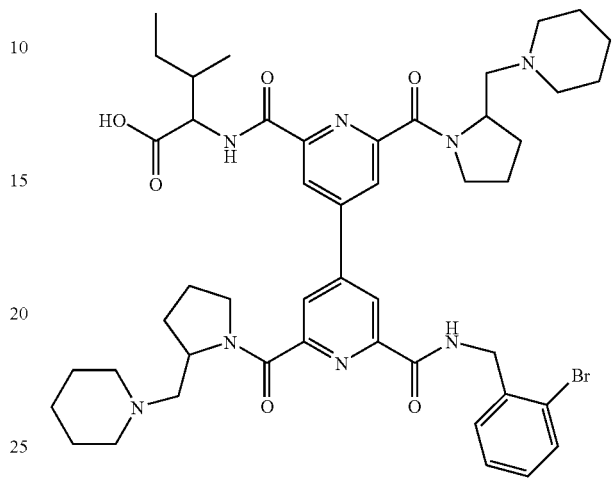

wherein: compound 19 is derived from S-amines.

Compound 20, which interrupts CD40:CD154 interaction, is a compound according to Formula (II), compound 20 being represented by the formula:

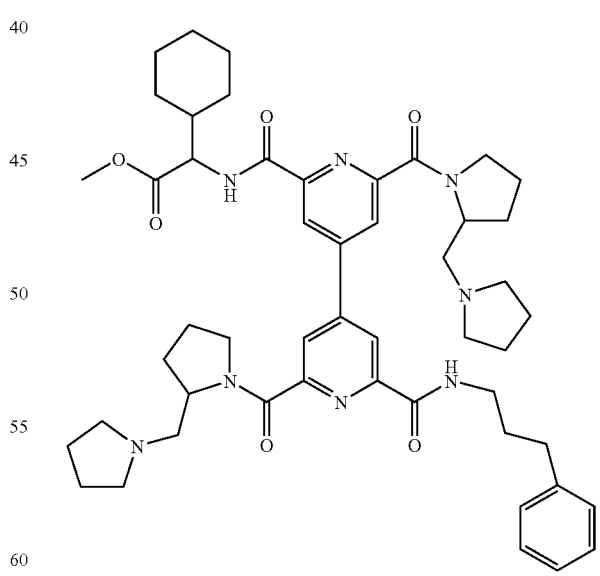

wherein: compound 20 is derived from S-amines.

Compound 21, which interrupts CD40:CD154 interaction, is a compound according to Formula (II), compound 21 being represented by the formula:

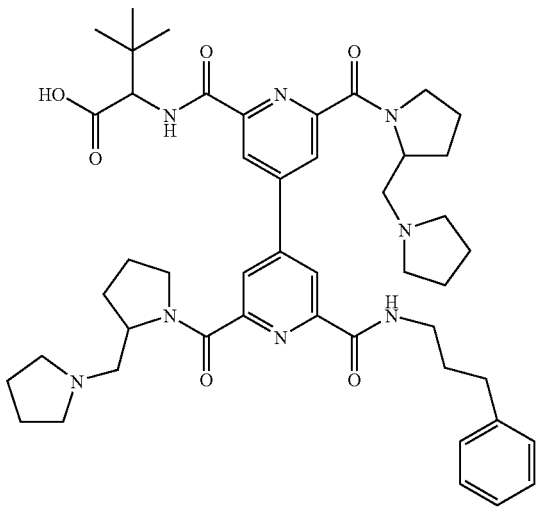

wherein: compound 21 is derived from S-amines.

In a preferred embodiment, this invention provides a compound of Formula (I), (II) or (III), wherein said compound binds CD154 specifically, and preferably interrupts CD40:CD154 interaction. Preferably these compounds have an $IC_{50}$ for CD40:CD154 interruption of less than or equal to approximately 310 μM; more preferably less than or equal to approximately 125 μM; and even more preferably less than or equal to approximately 50 μM.

In a more preferred embodiment, the invention provides a compound of Formula (I), (II) or (III), wherein said compound binds CD154 specifically; is a CD40:CD154 binding interrupter, and is not a TNF-α:TNFRp60 binding interrupter (i.e., does not bind to TNF-α and is not a TNF-α:TNFRp60 binding interrupter). Preferably, these compounds have an $IC_{50}$ for CD40:CD154 binding interruption of less than approximately 125 μM and an $IC_{50}$ for TNF-α(:TNFRp60 of more 125 μM.

$IC_{50}$, as used herein, is the concentration at which a compound interrupts the interaction of a protein and its receptor to 50% interaction in the assay shown in Example 7 (for interruption of CD40:CD154 interaction) and Example 8 (for interruption of TNFα:TNFRp60 interaction). Examples of such protein and receptor pairs are CD40:CD154 and TNF-α:TNFRp60.

Compounds 4–6 and 11 were shown to have $IC_{50}$ for CD40:CD154 binding interruption in the A range (less than 50 μM). Compounds 1, 7–10 and 13 were shown to have $IC_{50}$ for CD40:CD154 binding interruption in the B range (50 μM to 125 μM). Compounds 2–3 were shown to have $IC_{50}$ for CD40:CD154 binding interruption in the C range (greater than 125 μM). In addition, compounds 12, 14 and 16–21 are considered to have $IC_{50}$ for CD40:CD154 binding interruption in the B range (50 μM to 125 μM), and compound 15 in the A range (less than 50 μM). Compounds 1–4 were shown to have $IC_{50}$ of greater than 125 μM for TNF-α:TNFRp60 binding interruption. Table I lists the $IC_{50}$, for CD40:CD154 binding interruption and the mass spectrometry data for these twenty-one compounds.

TABLE I

| Compound | IC50 | Mass Spec* ** |
|---|---|---|
| 1 | B | 443.16 ((M + 2)/2) |
| 2 | C | 434.22 ((M + 2)/2) |
| 3 | C | 434.22 ((M + 2)/2) |
| 4 | A | 861.4 (M + 1) |
| 5 | A | 469.3 ((M + 2)/2) |
| 6 | A | 455.23 ((M + 2)/2) |
| 7 | B | 906.45 (M + 1) |
| 8 | B | 876.43 (M + 1) |
| 9 | B | 876 (M + 1) |
| 10 | B | 953 (M + 1) |
| 11 | A | 982.24 (M + 1) |
| 12 | B | 430.42 ((M + 2)/2) |
| 13 | B | 442.24 ((M + 2)/2) |
| 14 | B | 470.22 ((M + 2)/2) |
| 15 | A | 438.25 ((M + 2)/2) |
| 16 | B | 430.29 ((M + 2)/2) |
| 17 | B | 417 ((M + 2)/2) |
| 18 | B | 485 ((M + 2)/2) |
| 19 | B | 457 ((M + 2)/2) |
| 20 | B | 438.27 ((M + 2)/2) |
| 21 | B | 418.24 ((M + 2)/2) |

*M is for molecular mass.
**The formulas in the parenthesis show what the numbers represent.

The chemical syntheses of compounds 4, 7–11 are shown in Examples 1–6. A person skilled in the art would appreciate that the other compounds (compounds 1–3, 5–6 and 12–21) may be synthesized from intermediates and/or products disclosed in Examples 1–6 by routine methods. The skilled artisan would also appreciate that other routine methods may be used to synthesize these compounds. It should be understood that a person skilled in the art can synthesize any compound of Formula (I), (II) or (III) using conventional methods.

A specific assay to determine whether a compound interrupts CD40:CD154 interaction is shown in Example 7. A specific assay to determine whether a compound interrupts TNF-α:TNFRp60 interaction is shown in Example 8. Other well-known assays may be used for both determinations. One such assay is shown to determine whether a compound interrupts CD40:CD154 interruption is shown in Example 9. The interaction of CD40 and CD154 results in up-regulation of I-CAM1. A CD40:CD154 binding interrupter inhibits that up-regulation.

Conditions Associated with Inappropriate CD154 Induced Activation in a Subject

The CD40:CD154 binding interrupter compounds provided by this invention can be used to prevent or treat subjects having conditions associated with inappropriate CD154 induced activation. Treating a condition associated with inappropriate CD154 induced activation in a subject includes, inter alia, attenuating severity of the condition, suppressing effects of the condition, inhibiting the condition and reversing the condition.

Examples of conditions associated with inappropriate CD154 mediated activation in a subject, include, inter alia: an unwanted immune response, an unwanted inflammatory response, an autoimmune disease, an allergy, an inhibitor response to a therapeutic agent, rejection of a donor organ and a B cell cancer.

Examples of conditions associated with inappropriate CD154 mediated activation in a subject, include, inter alia: systemic lupus erythematosis, lupus nephritis, lupus neuritis, asthma, chronic obstructive pulmonary disease, bronchitis, emphysema, multiple sclerosis, uveitis, Alzheimer's disease, traumatic spinal cord injury, stroke, atherosclerosis, coronary restenosis, ischemic congestive heart failure, cirrhosis, hepatitis C, diabetic nephropathy, glomerulonephritis, osteoarthritis, rheumatoid arthritis, psoriasis, atopic dermatitis, systemic sclerosis, radiation-induced fibrosis, Crohn's disease, ulcerative colitis, multiple myeloma and cachexia.

Subjects

The CD40:CD154 binding interrupter compounds provided by this invention can be administered for treatment or prophylaxis to any mammalian subject suffering from or about to suffer a condition associated with inappropriate CD154 activation. Preferably, the subject is a primate, more preferably a higher primate, most preferably a human. In other embodiments, the subject may be a mammal of commercial importance, or a companion animal or other animal of value, such as a member of an endangered species. Thus, a subject may be, inter alia, sheep, horses, cattle, goats, pigs, dogs, cats, rabbits, guinea pigs, hamsters, gerbils, rats and mice.

Route of Administration

The CD40:CD154 binding interrupter compounds provided by this invention may be administered in any manner which is medically acceptable. Depending on the specific circumstances, local or systemic administration may be desirable. Local administration may be, for example, by subconjunctival administration. Preferably, the interrupter compound is administered via an oral, an enteral, or a parenteral route such as by an intravenous, intraarterial, subcutaneous, intramuscular, intraorbital, intraventricular, intraperitoneal, subcapsular, intracranial, intraspinal, topical or intranasal injection, infusion or inhalation. The interrupter compound also may be administered by implantation of an infusion pump, or a biocompatible or bioerodiable sustained release implant, into the subject.

Dosages and Frequency of Treatment

Generally, the methods described herein involve administration of the CD40:CD154 binding interrupter compounds at desired intervals (e.g., daily, twice weekly, weekly, biweekly, monthly or at other intervals as deemed appropriate) over at least a two- or three-week period. The administration schedule is adjusted as needed to treat the condition associated with inappropriate CD154 activation in the subject. A particular treatment regime can be repeated, in the event of a subsequent episode of illness.

The amount and frequency of dosing for any particular CD40:CD154 binding interrupter compound to be administered to a patient for a given immunological disease associated with inappropriate CD154 induced activation is within the skills and clinical judgement of ordinary practitioners of the medical and pharmaceutical arts. The general dosage and administration regime may be established by preclinical and clinical trials, which involve extensive but routine studies to determine the optimal administration parameters of the compound. Even after such recommendations are made, the practitioner will often vary these dosages for different subjects based on a variety of considerations, such as the individual's age, medical status, weight, sex, and concurrent treatment with other pharmaceuticals. Determining the optimal dosage and administration regime for each synthetic CD40:CD154 binding interrupter compound used is a routine matter for those of skill in the medical and pharmaceutical arts.

Generally, the frequency of dosing may be determined by an attending physician or similarly skilled practitioner, and might include periods of greater dosing frequency, such as at daily or weekly intervals, alternating with periods of less frequent dosing, such as at monthly or longer intervals.

To exemplify dosing considerations for a CD40:CD154 binding interruptor, the following examples of administration strategies are given for an anti-CD154 mAb. Such illustrative dosing amounts could easily be adjusted for other types of anti-CD154 compounds according to the present invention. In general, single dosages of between about 0.05 and about 50 mg/kg patient body weight are contemplated, with dosages most frequently in the 1–20 mg/kg range. For acute treatment, such as before or at the time of transplantation, or in response to any evidence that graft rejection is beginning, an effective dose of a representative antibody (such as mAb 5c8), which may serve as a guideline for the dosages of a compound according to this invention, ranges from about 1 mg/kg body weight to about 20 mg/kg body weight, administered daily for a period of about 1 to 5 days, preferably by bolus intravenous administration. The same dosage and dosing schedule may be used in the load phase of a load-maintenance regimen, with the maintenance phase involving intravenous or intramuscular administration being patterned on that of an anti-CD154 mAb in a range of about 0.1 mg/kg body weight to about 20 mg/kg body weight, for a treatment period of anywhere from weekly to 3 month intervals. Chronic treatment may also be carried out by a maintenance regimen, patterned on that in which antibodies are administered by intravenous or intramuscular route, in a range of about 0.1 mg/kg body weight to about 20 mg/kg body weight, with interdose intervals ranging from about 1 week to about 3 months. In addition, chronic treatment may be effected by an intermittent bolus intravenous regimen, patterned on that in which between about 1.0 mg/kg body weight and about 100 mg/kg body weight of an anti-CD154 mAb are administered, with the interval between successive treatments being from 1 to 6 months. For all except the intermittent bolus regimen, administration may also be by oral, pulmonary, nasal or subcutaneous routes.

For treatment, a CD40:CD154 binding interrupter compound can be formulated in a pharmaceutical or prophylactic composition which includes, respectively, a pharmaceutically or prophylactically effective amount of the CD40:CD154 binding interrupter compound dispersed in a pharmaceutically acceptable carrier. In some embodiments, the pharmaceutical or prophylactic composition can also include a pharmaceutically or prophylactically effective amount of another immunosuppressive or immunomodulatory compound, including without limitation: an agent that interrupts T cell costimulatory signaling via CD28 (e.g., CTLA4-Ig), CD80 or CD86; an agent that interrupts calcineurin signaling (e.g., cyclosporin, a macrolide such tacrolimus, formerly known as FK506); a corticosteroid; or an antiproliferative agent (e.g., azathioprine). Other therapeutically effective compounds suitable for use with the CD40:CD154 binding interrupter include rapamycin (also known as sirolimus); mycophenolate mofetil (MMF), mizoribine, deoxyspergualin, brequinar sodium, leflunomide, azaspirane and the like.

Combination therapies according to this invention for treatment of a condition associated with inappropriate CD154 activation in a subject include the use of a synthetic CD40:CD154 binding interrupter compound together with agents targeted at B cells, such as anti-CD19, anti-CD28 or anti-CD20 antibody (unconjugated or radiolabeled), IL-14 antagonists, LJP394 (LaJolla Pharmaceuticals receptor blocker), IR-1116 (Takeda small molecule) and anti-Ig idiotype monoclonal antibodies. Alternatively, the combinations may include T cell/B cell targeted agents, such as CTLA4Ig, IL-2 antagonists, IL-4 antagonists, IL-6 antagonists, receptor antagonists, anti-CD80/CD86 monoclonal antibodies, TNF, LFA1/ICAM antagonists, VLA4/VCAM antagonists, brequinar and IL-2 toxin conjugates (e.g., DAB), prednisone, anti-CD3 mAb (OKT3), mycophenolate mofetil (MMF), cyclophosphamide, and other immunosuppressants such as calcineurin signal blockers, including without limitation, tacrolimus (FK506). Combinations may also include T cell targeted agents, such as CD4 antagonists, CD2 antagonists and anti-IL-12 antibodies.

The immunomodulatory compound that may be co-administered with a synthetic CD40:CD154 binding interrupter compound to a subject with a condition associated with inappropriate CD154 activation may be an antibody that specifically binds to a protein selected from the group consisting of CD45, CD2, IL2R, CD4, CD8 and RANK Fc.

Formulation

In general, CD40:CD154 binding interrupter compounds of this invention are suspended, dissolved or dispersed in a pharmaceutically acceptable carrier or excipient. The resulting therapeutic composition does not adversely affect the recipient's homeostasis, particularly electrolyte balance. Thus, an exemplary carrier comprises normal physiologic saline (0.15M NaCl, pH 7.0 to 7.4). Other acceptable carriers are well known in the art and are described, for example, in *Remington's Pharmaceutical Sciences*, Gennaro, ed., Mack Publishing Co., 1990. Acceptable carriers can include biocompatible, inert or bioabsorbable salts, buffering agents, oligo- or polysaccharides, polymers, viscoelastic compounds, such as hyaluronic acid, viscosity-improving agents, preservatives, and the like.

A CD40:CD154 binding interrupter compound provided by this invention may be administered in a pharmaceutically effective, prophylactically effective or therapeutically effective amount, which is an amount sufficient to produce a detectable, preferably medically beneficial effect on a subject at risk for or afflicted with a condition associated with inappropriate CD154 activation. Medically beneficial effects include preventing, inhibiting, reversing or attenuating deterioration of, or detectably improving, the subject's medical condition.

EXAMPLES

The following examples illustrate preferred embodiments of this invention related to novel CD40:CD154 binding interrupter compounds and the use of these compounds to treat or prevent conditions associated with inappropriate CD154 activation in a subject. These examples should not be construed as limiting: the examples are included for the purposes of illustration only.

The following method describes the preparation of a mass-coded combinatorial library and the screening technology applied to obtain CD40:CD154 binding interrupter compounds disclosed in this invention. This method is advantageous because it can be used to identify chemical compounds that bind tightly to any biomolecule of interest, such as CD154. The screening technologies described can be miniaturized to provide massive parallel screening capabilities.

Methods for producing mass-coded combinatorial libraries are disclosed in PCT patent application WO99/35109, published Jul. 15, 1999, the disclosure of which is hereby incorporated by reference.

One method according to WO99/35109 allows identification of a member or members of a mass-coded combinatorial library which are ligands for a biomolecule, for example, a protein such as CD154. This method comprises the steps of: (1) contacting the biomolecule with the mass-coded molecular library, whereby members of a mass-coded molecular library which are ligands for the biomolecule bind to the biomolecule to form biomolecule-ligand complexes and members of the mass-coded library which are not ligands for the biomolecule remain unbound; (2) separating the biomolecule-ligand complexes from the unbound members of the mass-coded molecular library; (3) dissociating the biomolecule-ligand complexes; and (4) determining the molecular mass of each ligand to identify the set of n peripheral moieties present in each ligand.

The method of WO99/35109 allows rapid production of mass-coded combinatorial libraries comprising large numbers of compounds. The mass-coding enables the identification of individual combinations of scaffold and peripheral moieties by molecular mass. The resulting libraries also allow the rapid identification of compounds which are ligands for a given biomolecule, such as CD154.

One of the methods of WO99/35109 allows the preparation of a mass-coded set of compounds, such as a mass-coded combinatorial library. These compounds are of the general formula $X(Y)_n$, wherein X is a scaffold, each Y is a peripheral moiety and n is 4. The term "scaffold", as used in WO99/35109 and herein, refers to a molecular fragment to which four peripheral moieties are attached via a covalent bond. The scaffold is a molecular fragment which is common to each member of the mass-coded set of compounds. The term "peripheral moiety", as used in WO99/35109 and herein, refers to a molecular fragment which is bonded to a scaffold. Each member of the set of mass-coded compounds will include a combination of four peripheral moieties bonded to the scaffold and this set of compounds forms a mass coded combinatorial library.

The term "mass" or "molecular mass", as used in WO99/35109 and herein in relation to combinatorial libraries, refers to the exact mass of a molecule or collection of chemical moieties in which each atom is the most abundant naturally occurring isotope for the particular element. Exact masses and their determination by mass spectrometry are discussed by Pretsch et al., *Tables of Spectral Data for Structure Determination of Organic Compounds*, second edition, Springer-Verlag (1989), and Holden et al., *Pure Appl. Chem.* 55 : 1119–1136 (1983), the contents of each of which are incorporated herein by reference in their entirety.

A scaffold precursor represented by Formula IV, having four reactive groups which are capable of reacting with a peripheral moiety precursor reactive group to form a covalent bond was chosen as a starting material for the synthesis of compounds according to this invention. That scaffold precursor, used in Scheme I (infra), is described in K. E. Pryor et. al. *Tetrahedron* 54: 4107–4124 (1998), the disclosure of which is incorporated by reference herein. Scaffold precursors V–VI, respectively used in Schemes II and III (infra) were synthesized according to the reaction scheme shown by Pryor et. al., followed by additional modification with conventional chemical protecting techniques.

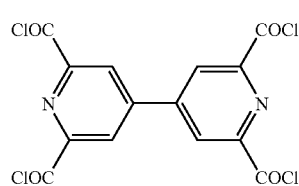

Formula IV

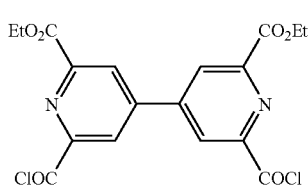

Formula V

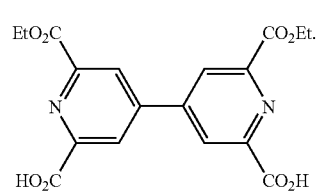

Formula VI

A peripheral moiety precursor is a compound which includes a reactive group which is complementary to the reactive groups of the scaffold precursor. In addition to the reactive group, a peripheral moiety precursor can include a wide variety of structural features. For example, the peripheral moiety precursor can include one or more functional groups in addition to the reactive group. Any additional functional group should be appropriately masked or not interfere with the reaction between the scaffold precursor and the peripheral moiety precursor. Suitable protecting groups for masking are known in the art for a variety of functional groups (Greene and Wuts, *Protective Groups in Organic Synthesis*, second edition, New York: John Wiley and Sons (1991), and third edition, New York: John Wiley and Sons (1999), the disclosures of both of which are incorporated herein by reference). Particularly useful protecting groups include t-butyl esters and ethers, acetals, trityl ethers and amines, acetyl esters, trimethylsilyl ethers and trichloroethyl ethers and esters. In addition, two peripheral moiety precursors should not react together under the conditions employed. For example, a subset of peripheral moiety precursors can include, in addition to the reactive groups, functionalities selected from groups spanning a range of charge, hydrophobicity/hydrophilicity, and sizes. For example, the peripheral moiety precursor can include a negative charge, a positive charge, a hydrophilic group or a hydrophobic group.

For the present purposes, two reactive groups are complementary if they are capable of reacting together to form a covalent bond. In a preferred embodiment, the bond forming reactions occur rapidly under ambient conditions without substantial formation of side products. Preferably, a given reactive group will react with a given complementary reactive group exactly once.

Complementary electrophilic and nucleophilic groups include any two groups which react via nucleophilic substitution under suitable conditions to form a covalent bond. An example of a suitable electrophilic group is an acid chloride. A suitable nucleophilic group include primary and secondary amino groups.

Illustrated below in Table II are examples of suitable peripheral moiety precursors. Each peripheral moiety precursor includes a primary or secondary amino group which reacts with the scaffold precursor to form an amide bond.

TABLE II

| BB ID* | MOLSTRUCTURE | Mass | BB ID* | MOLSTRUCTURE | Mass | BB ID* | MOLSTRUCTURE | Mass |
|---|---|---|---|---|---|---|---|---|
| 11 | (4-benzylpiperidine) | 175.136 | 61 | (benzylamine) | 107.073 | 138 | (2-chlorophenethylamine) | 155.05 |
| 13 | (cyclohexylmethylamine) | 113.12 | 115 | (glutamic acid) | 147.053 | 140 | (4-piperidinopiperidine) | 168.163 |
| 15 | ((R)-1-cyclohexylethylamine) | 127.136 | 116 | (sarcosine) | 75.032 | 141 | (N,N-diethylethylenediamine) | 144.163 |
| 16 | ((S)-1-cyclohexylethylamine) | 127.136 | 117 | (isoleucine) | 131.095 | 157 | (N,N-dimethylethylenediamine) | 116.131 |
| 17 | (cyclopentylamine) | 85.0891 | 118 | (valine) | 131.095 | 161 | (phenylalanine methyl ester) | 179.095 |

TABLE II-continued
| BB ID* | MOLSTRUCTURE | Mass | BB ID* | MOLSTRUCTURE | Mass | BB ID* | MOLSTRUCTURE | Mass |
|---|---|---|---|---|---|---|---|---|
| 27 | 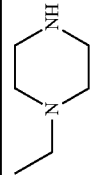 | 114.116 | 119 |  | 146.106 | 201 |  | 119.058 |
| 36 | 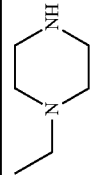 | 75.0684 | 120 | 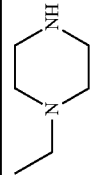 | 165.079 | 204 | 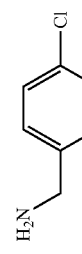 | 135.105 |
| 45 | 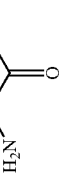 | 87.0684 | 122 |  | 115.063 | 214 | 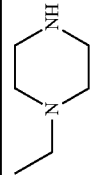 | 141.035 |
| 50 | 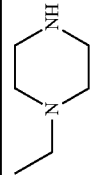 | 220.121 | 124 | 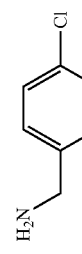 | 105.043 | 226 |  | 31.0422 |
| 52 |  | 154.147 | 127 | 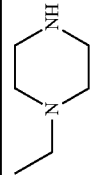 | 117.079 | 243 | 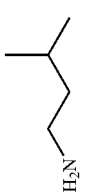 | 87.1048 |

TABLE II-continued
| BB ID* | MOLSTRUCTURE | Mass | BB ID* | MOLSTRUCTURE | Mass | BB ID* | MOLSTRUCTURE | Mass |
|---|---|---|---|---|---|---|---|---|
| 245 | 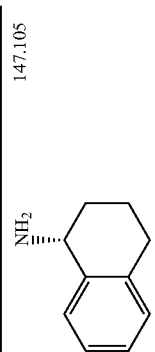 | 102.116 | 300 | 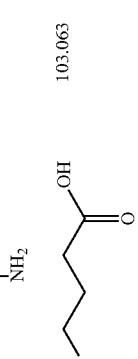 | 135.105 | 387 | 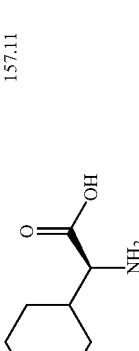 | 147.105 |
| 256 | 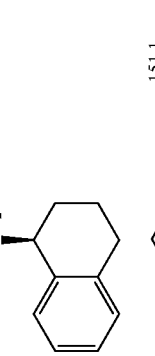 | 151.063 | 301 | 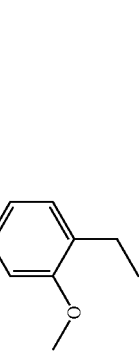 | 137.084 | 388 |  | 147.105 |
| 270 | 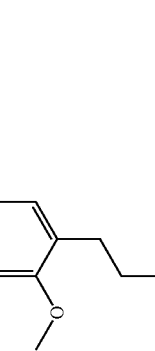 | 89.0477 | 307 | 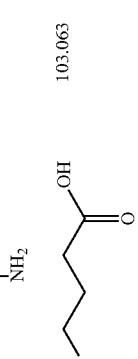 | 165.079 | 396 | 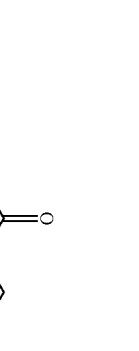 | 151.1 |
| 277 | 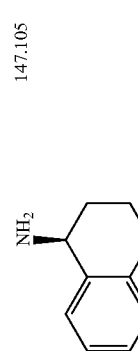 | 184.984 | 315 | 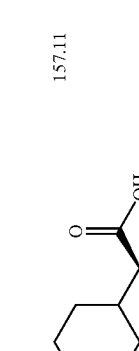 | 200.062 | 419 | 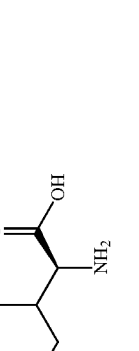 | 103.063 |
| 283 | 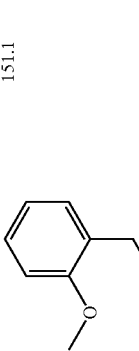 | 179.095 | 318 | 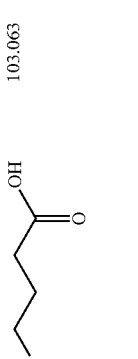 | 145.11 | 424 |  | 157.11 |

TABLE II-continued

| BB ID* | MOLSTRUCTURE | Mass | BB ID* | MOLSTRUCTURE | Mass | BB ID* | MOLSTRUCTURE | Mass |
|---|---|---|---|---|---|---|---|---|
| 286 | | 133.089 | 323 | | 151.063 | 465 | | 111.08 |
| 287 | | 133.089 | 350 | | 116.131 | 466 | | 160.1 |
| 288 | | 137.084 | 353 | | 130.147 | 475 | | 101.084 |
| 290 | | 165.115 | 370 | | 127.046 | 500 | | 185.061 |
| 292 | | 135.105 | 385 | | 101.048 | 514 | | 142.111 |
| 533 | | 114.116 | 587 | | 103.063 | 597 | | 130.111 |

TABLE II-continued

| BB ID* | MOLSTRUCTURE | Mass | BB ID* | MOLSTRUCTURE | Mass | BB ID* | MOLSTRUCTURE | Mass |
|---|---|---|---|---|---|---|---|---|
| 551 | (prolinamide structure) | 114.079 | 588 | (piperidinylmethyl-piperidine) | 182.178 | 598 | (iminodibenzyl-propyl-methylamine) | 266.178 |
| 564 | NH$_3$ | 17.0266 | 589 | (N,N-dimethyl-piperidinylmethylamine) | 142.147 | 599 | (valinamide) | 116.095 |
| 580 | (glutamine) | 146.069 | 590 | (arginine) | 174.112 | 600 | (biphenylmethylamine) | 183.105 |
| 581 | (asparagine) | 132.054 | 591 | (tyrosine) | 181.074 | 601 | (4-bromophenyl-propylamine) | 213.015 |
| 582 | (histidine) | 155.07 | 592 | (methionine) | 149.051 | 602 | (isoleucine) | 131.095 |

TABLE II-continued
| BB ID* | MOLSTRUCTURE | Mass | BB ID* | MOLSTRUCTURE | Mass | BB ID* | MOLSTRUCTURE | Mass |
|---|---|---|---|---|---|---|---|---|
| 583 |  | 211.136 | 593 |  | 156.159 | 603 |  | 171.126 |
| 584 |  | 133.089 | 594 | 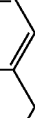 | 157.089 | 604 | 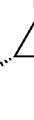 | 117.079 |
| 585 | 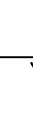 | 149.12 | 595 |  | 149.12 | 605 |  | 184.121 |
| 586 |  | 185.142 | 596 | 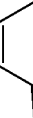 | 164.095 | 606 |  | 170.142 |
| 607 |  | 182.142 | 617 |  | 213.015 | 634 |  | 210.064 |

TABLE II-continued

| BB ID* | MOLSTRUCTURE | Mass | BB ID* | MOLSTRUCTURE | Mass | BB ID* | MOLSTRUCTURE | Mass |
|---|---|---|---|---|---|---|---|---|
| 608 | (piperidine-pyrrolidine structure) | 168.163 | 618 | (3-bromophenylpropylamine) | 213.015 | 635 | (cyclohexyl glycine) | 157.11 |
| 609 | (pyrrolidine carbonyl-pyrrolidine) | 168.126 | 619 | (3,4-dichlorophenylpropylamine) | 203.027 | 636 | (dimethyl-hydroxyphenyl alanine) | 209.105 |
| 610 | (dimethylaminomethyl pyrrolidine) | 128.131 | 625 | (tert-leucine) | 131.095 | 638 | (cyclohexyl glycine) | 157.11 |
| 611 | (thiazolidine carbonyl-pyrrolidine) | 186.083 | 628 | (cis-cinnamylamine) | 133.089 | 639 | (leucine) | 131.095 |
| 612 | (thiazolidinylmethyl pyrrolidine) | 172.103 | 629 | (trans-cinnamylamine) | 133.089 | | | |

TABLE II-continued

| BB ID* | MOLSTRUCTURE | Mass | BB ID* | MOLSTRUCTURE | Mass | BB ID* | MOLSTRUCTURE | Mass |
|---|---|---|---|---|---|---|---|---|
| 613 | | 210.173 | 630 | | 129.079 | | | |
| 614 | | 196.194 | 631 | | 143.095 | | | |
| 615 | | 154.111 | 632 | | 155.095 | | | |
| 616 | | 140.131 | 633 | | 177.079 | | | |

*Identification number of the peripheral moiety precursors.

The compounds within the combinatorial library set are mass-coded as a result of the selection of a subset of suitable peripheral moiety precursors. The mass-coded set of compounds is synthesized in solution as a combinatorial library.

In one embodiment, the scaffold precursor is contacted with all members of the peripheral moiety precursor subset simultaneously. In general, a scaffold precursor having four reactive groups will be contacted with at least about 4 molar equivalents relative to the scaffold precursor of peripheral moiety precursors from the selected subset. For example, the scaffold precursor can be contacted with a solution comprising each member of the subset in approximately equal concentrations. In one embodiment, the reaction protocol shown below (Scheme I) was used.

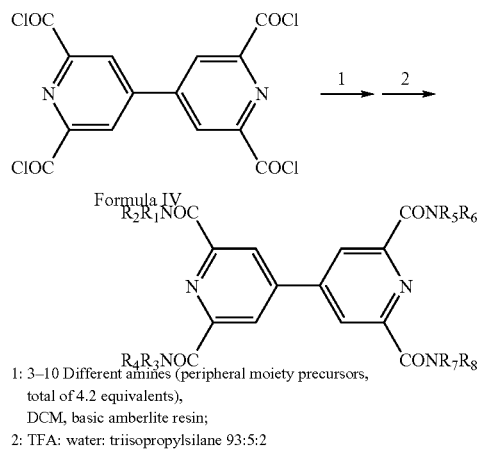

1: 3–10 Different amines (peripheral moiety precursors, total of 4.2 equivalents), DCM, basic amberlite resin;
2: TFA: water: triisopropylsilane 93:5:2

In another embodiment, the reaction protocol shown below (Scheme II) was used.

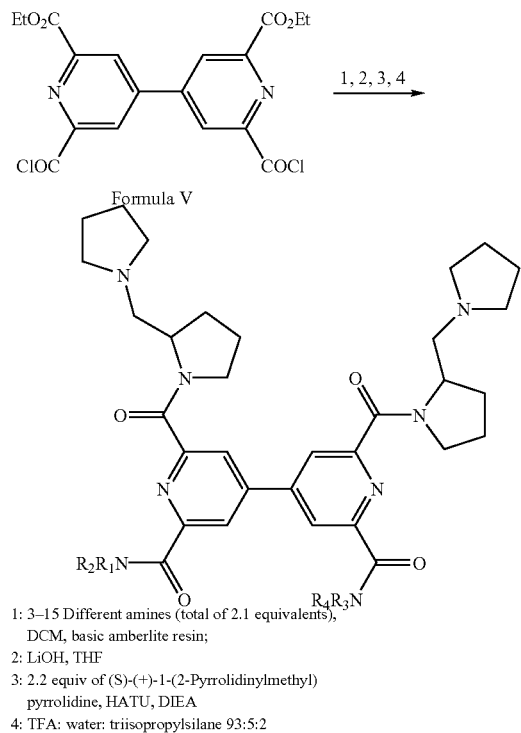

1: 3–15 Different amines (total of 2.1 equivalents), DCM, basic amberlite resin;
2: LiOH, THF
3: 2.2 equiv of (S)-(+)-1-(2-Pyrrolidinylmethyl) pyrrolidine, HATU, DIEA
4: TFA: water: triisopropylsilane 93:5:2

In another embodiment, the reaction protocol shown below (Scheme III) was used.

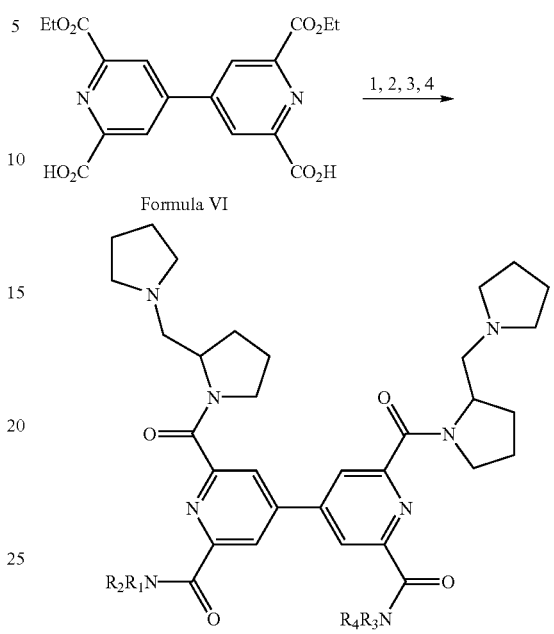

1: 3–15 Different amines (total of 2.1 equivalents), HATU, DIEA
2: LiOH, THF
3: 2.2 equiv of (S)-(+)-1-(2-Pyrrolidinyl)pyrrolodine, HATU, DIEA
4: TFA: water: triisopropylsilane 93:5:2

Following the reaction of each scaffold precursor reactive group with a peripheral moiety precursor, any peripheral moiety having a protected, additional functional group can be deprotected using methods known in the art.

The ability to identify individual scaffold plus peripheral moiety combinations derived from such a mixture is a consequence of the mass-coding of the library and the ability of mass spectrometry to identify a molecular mass. This allows the identification of individual scaffold plus peripheral moiety combinations within the set which have a particular activity, such as binding to a particular biomolecule, such as CD154.

In one embodiment, a method is provided for identifying a compound or compounds within a mass-coded combinatorial library which bind to, or are ligands for, a biomolecule, such as a CD154. The mass-coded combinatorial library can be produced, for example, by the method disclosed above. The target biomolecule, such as CD154, is contacted with the mass-coded combinatorial library, and, if any members of the library are ligands for a target biomolecule, biomolecule-ligand complexes form. Compounds which do not bind the target biomolecule are separated from the biomolecule-ligand complexes. The biomolecule-ligand complexes are dissociated and the ligands are separated and their molecular masses are determined by mass spectrometry. Due to the mass coding of the combinatorial library, a given molecular mass is characteristic of a unique combination of peripheral moieties or only a small number of such combinations. Thus, a ligand's molecular mass allows the determination of its composition.

Once single ligands are identified by the above-described process, various levels of analysis can be applied to yield SAR information and to guide further optimization of the affinity, specificity and bioactivity of the ligand. For ligands derived from the same scaffold, three-dimensional molecular modeling can be employed to identify significant structural features common to the ligands, thereby generating families of small-molecule ligands that presumably bind at a common site on the target biomolecule.

To identify a consensus, highest affinity ligand for a particular binding site, this analysis should include a ranking of the members of a given ligand family with respect to their affinities for the target. This process can provide this information by identifying both low and high affinity ligands for a target biomolecule in one experiment.

Given that each mass-coded set of compounds is synthesized with a limited number of peripheral moiety precursors, the described approach can, in certain cases, identify a superior ligand which combines structural features of molecules synthesized in separate libraries.

When possible, the analysis of ligand structural features is based on information regarding the target biomolecule's structure, wherein the hypothetical consensus ligand is computationally docked with the putative binding site. Further computational analysis can involve a dynamic search of multiple lowest energy conformations, which allows comparison of high affinity ligands that are derived from different scaffolds. The end goal is the identification of both the optimal functionality and the optimal vectorial presentation of the peripheral moieties that yields the highest binding affinity/specificity. This may provide the basis for the synthesis of an improved, second-generation scaffold.

An advantage of the method discussed above is that it can be used to identify chemical compounds that bind tightly to any biomolecule of interest, such as CD154.

Screening a Mass-Coded Combinatorial Library for Novel CD40:CD154 Binding Interruptors Methods for identifying compounds in a chemical mixture are described in the PCT patent application WO00/22649, published Apr. 20, 2000, the disclosure of which is hereby incorporated by reference. These methods and the methods disclosed in WO99/35109 were used to identify compounds that bind CD154 from a mixture of compounds (a mass-coded combinatorial library).

The WO00/22649 application relates generally to Mass Spectrographic analysis, and more specifically to the identification of organic compounds in complex mixtures of organic compounds.

The mass coded combinatorial library was prepared by treating the reactive scaffold precursors (shown in Formulae IV–VI) with pools of building blocks shown in Table II using the reaction protocols shown in Schemes I–III.

The mass-coded combinatorial library was screened for novel CD40:CD154 binding interrupters according the the methods discussed herein. The library was first screened for compounds that bind CD154. Those compounds that interact with CD154 were identified, isolated and their chemical compositions were verified with mass spectrometry. The compounds that interact with CD154 can then each be synthesized on a larger scale following the method described below.

The compounds were then screened for the ability to inhibit CD40:CD154 interaction. A person skilled in the art is well aware of conventional assays to assess whether the compounds designed according to this invention bind specifically to CD154 and whether the compounds of this invention interrupt CD40:CD154 interaction. These assays, for example, detect the extent to which B cells are activated by activated T cells via the interaction between CD154 and CD40. For example, monitoring of CD23 levels on B cells, or secretion of immunoglobulins by B cells is indicative of activation of B cells by activated T cells via the interaction between CD40 and CD154. See, e.g., U.S. Pat. No. 5,474,771. Accordingly, examples of such assays are: the assay of Example 7, an in vitro assay for T cell activation of B cells; an in vitro assay for immunoglobulin production by B cells and an in vivo assay for inhibition of a humoral immune response.

Once a compound is discovered by the methods described above, substitutions may then be made by conventional methods in some of its atoms or side groups to further improve or modify its binding and/or inhibition properties. Such substituted chemical compounds may then be analyzed for binding to CD154 and inhibition of CD40:CD154 interaction.

Example 1

Chemical Synthesis of Compound 7

Step 1: A mixture of chelidamic acid monohydrate (1.00 g, 4.97 mmol) and phosphorus pentabromide (8.45 g, 19.6 mmol) was warmed to 90° C. for 3 hours (h). Chloroform (100 mL) was added to the warm reaction mixture and the resulting slurry was filtered. The filtrate was concentrated in vacuo to give a pink solid. The solid was dissolved in ethanol (vigorous reaction), stirred for 0.5 h and then concentrated in vacuo to give a yellow solid. The solid was dissolved in ether (250 mL), washed with saturated aqueous sodium bicarbonate (50 mL×2), dried ($MgSO_4$) and concentrated in vacuo to give 1.30 g of a white solid.

Step 2: A solution of KOH (0.83 g, 3.31 mmol) in anhydrous ethanol (40 mL) was added dropwise to a solution of the compound from step 1 (3.85 g, 12.7 mmol) in anhydrous ethanol (100 mL) over the course of 3 h. A white precipitate formed. The unstirred slurry was allowed to sit at room temperature (RT) for 7 h and then at 0° C. overnight. The slurry was filtered and the resulting white solid dissolved in water (100 mL), cooled to 0° C. and acidified to pH 1 with 1N HCl. The slurry was filtered and the resulting white solid dried in vacuo to give 3.00 g white solid.

Step 3: Catalytic DMF and 2.0 M oxalyl chloride/dichloromethane (4.5 mL, 9.0 mmol) were added to a solution of the compound from step 2 (1.20 g, 4.40 mmol) in dichloromethane at RT. The reaction solution was stirred until bubbling ceased and was then concentrated in vacuo. The residue was dissolved in toluene (20 mL) and added dropwise to a solution of L-cyclohexylglycine tbutyl ester.HCl (1.20 g, 4.80 mmol) in pyridine (10 mL) at RT. The reaction was stirred overnight at RT, diluted with ether, washed with water, dried ($MgSO_4$) and concentrated in vacuo to give an oil. The oil was purified via flash column chromatography (95:5 methylene chloride/ethyl acetate) to give 1.01 g of a colorless oil.

Step 4: A solution of the compound from step 3 (0.500 g, 1.07 mmol), bis(pinacolate)diboran (0.300 g, 1.18 mmol), [1,1'-bis(diphenylphosphino)ferrocene]dichloropalladium (II).methylene chloride (0.026 g, 0.032 mmol) and potassium acetate (0.315 g, 3.21 mmol) in anhydrous DMF (7 mL) was warmed to 80° C. under a nitrogen atmosphere for 2 h. The reaction was then cooled to RT, diluted with ethyl acetate (70 mL), washed with 5% citric acid (25 mL), 5% sodium bicarbonate (25 mL) and water (25 mL), dried ($MgSO_4$) and concentrated in vacuo to give a brown oil.

Step 5: 3-Phenyl-1-propylamine (4.0 mL, 28.1 mmol) was added dropwise to concentrated nitric acid at 0° C. The reaction was allowed to warm to RT overnight. The reaction was warmed to 50° C. for 2 h, concentrated nitric acid (10 mL) was added and the reaction was warmed for another 2 h at 500 C. The reaction was cooled to 0° C. and poured into ice water. The yellow precipitate was isolated via filtration, washed with water and air dried to give 1.30 g of a yellow solid. $^1$H NMR indicated formation of the para isomer only.

Step 6: Catalytic DMF and 2.0 M oxalyl chloride/dichloromethane (4.5 mL, 9.0 mmol) were added to a solution of the compound from step 2 (1.20 g, 4.40 mmol) in dichloromethane at RT. The reaction solution was stirred until bubbling ceased and concentrated in vacuo. The residue was dissolved in toluene (20 mL) and added dropwise to a solution of the compound from step 5 (1.20 g, 4.93 mmol) in pyridine (10 mL) at RT. The reaction was stirred overnight at RT, diluted with ether, washed with water, dried (MgSO$_4$) and concentrated in vacuo to give an oil. The oil was purified via flash column chromatography (90:10 methylene chloride/ethyl acetate) to give 0.51 g of a yellow solid.

Step 7: 2 M aqueous sodium carbonate (2.70 mL, 5.4 mmol) was added to a solution of the compound from step 4, the compound from step 6 (0.51 g, 1.17 mmol) and [1,1'-bis(diphenylphosphino)ferrocene]dichloropalladium (II).methylene chloride (0.026 g, 0.032 mmol) in anhydrous DMF. The reaction was warmed to 80° C. overnight. It was then cooled to RT, diluted with ethyl acetate, washed with water and brine, dried (MgSO$_4$) and concentrated in vacuo to give a brown oil.

Step 8: Lithium hydroxide was added to a solution of the compound from step 7 in 2:1 THF/water at RT. When all starting ester was consumed via HPLC analysis, the reaction was diluted with cold water and washed with ethyl acetate. The aqueous phase was saturated with ammonium chloride and extracted with THF. The combined organic phases were dried (MgSO$_4$) and concentrated in vacuo. The resulting solid was washed with water and air dried to give 1.20 g of a dark solid. (approx. 50% desired material)

Step 9: S-(+)-1-(2-pyrrolidinylmethyl)pyrrolidine (0.80 g, 5.2 mmol), HATU (2.0 g, 5.3 mmol) and diisopropylethyl amine (1.8 mL, 10.3 mmol) were added to a solution of the compound from step 8 (1.2 g) in anhydrous DMF (25 mL) at RT. The reaction was stirred at RT overnight. The volatiles were removed in vacuo, the residue dissolved in ethyl acetate and washed with water. The organic phase was dried (MgSO$_4$), concentrated in vacuo and purified via flash column chromatography (100:10:2 ethyl acetate/methanol/triethyl amine) to give 0.650 g of a brown solid.

Step 10: A solution of the compound from step 9 (0.030 g) in 2:1 TFA/methylene chloride (6 mL) was stirred at RT for 3 h. The reaction was then concentrated in vacuo and purified via reverse phase HPLC (acetonitrile/water) to give a white solid.

Example 2

Chemical Synthesis of Compound 8

Step 1: steps 1–9 of EXAMPLE 1 were carried out.

Step 2: Catalytic 10% Pd/C was added to a solution of the compound from step 1 (0.100 g) in ethyl acetate. The reaction was stirred under a hydrogen atmosphere (1 atm) overnight. The reaction was then centrifuged and the supernatant decanted and concentrated in vacuo.

Step 3: A solution of the compound from step 2 (0.020 g) in 2:1 TFA/methylene chloride (6 mL) was stirred at RT for 2 h. The reaction was then concentrated in vacuo and purified via reverse phase HPLC (acetonitrile/water) to give an off-white solid.

Example 3

Chemical Synthesis of Compound 4

Step 1: steps 1 and 2 of EXAMPLE 1 were carried out.

Step 2: Catalytic DMF and 2.0 M oxalyl chloride/dichloromethane (3.0 mL, 6.0 mmol) were added to a solution of the compound from step 1 (2.72 g, 2.64 mmol) in dichloromethane (20 mL) at RT. The reaction solution was stirred until bubbling ceased, diluted with toluene (40 mL) and reduced in volume in vacuo. A solution of 3-phenyl-1-propylamine (1.7 mL, 11.9 mmol) in pyridine (8 mL) was added and the resulting solution was stirred at RT overnight. The reaction solution was diluted with ethyl acetate (300 mL), washed with water (150 mL), 1N HCl (150 mL×3) and water (150 mL), dried (MgSO$_4$) and concentrated in vacuo to give an oil. The oil was dissolved in 1:1 saturated aqueous lithium hydroxide/THF and stirred overnight at RT. The reaction was then acidified with 1N HCl, extracted with ethyl acetate, dried (MgSO$_4$) and concentrated in vacuo to give 3.456 g of an oil.

Step 3: A solution of the compound from step 2 (3.456 g, 9.515 mmol), bis(pinacolate)diboran (2.658 g, 10.54 mmol), [1,1'-bis(diphenylphosphino)ferrocene]dichloropalladium (II).methylene chloride (1.029 g, 1.26 mmol) and potassium acetate (3.88 g, 39.5 mmol) in anhydrous DMF (60 mL) was warmed to 80° C. under a nitrogen atmosphere for 2.5 h. The reaction was then cooled to RT, diluted with ethyl acetate (500 mL) and extracted with 1N sodium hydroxide (200 mL). The aqueous phase was washed with ethyl acetate (250 mL×2), acidified with concentrated HCl to pH 0 and extracted with ethyl acetate (500 mL×2). The combined organic phases were dried (MgSO$_4$) and concentrated in vacuo to give an oil which was slurried with ether. The resultant light brown solid was filtered and air dried to give 1.48 g of product. The mother liquor was concentrated in vacuo to give 1.78 g of product.

Step 4: L-cyclohexylglycine tbutyl ester.HCl (1.717 g, 6.87 mmol), HATU (2.618 g, 6.89 mmol) and diisopropylethyl amine (4.00 mL, 23.0 mmol) were added to a solution of the compound from Example 1, step 2 (1.704 g, 6.24 mmol) in anhydrous DMF (10 mL) at RT. The reaction was stirred at RT for 2.5 h. The reaction was diluted with saturated aqueous sodium bicarbonate (50 mL) and extracted with ether (150+100 mL). The organic phases were washed with water (100+50 mL), dried (MgSO$_4$) and concentrated in vacuo to give 2.994 g of a yellow oil.

Step 5: Saturated aqueous lithium hydroxide (3 mL) was added to a solution of the compound from step 4 (2.994 g, 6.24 mmol) in THF (10 mL) at RT. After 1 h, saturated aqueous sodium bicarbonate (50 mL) was added. The slurry was then cooled to 0° C., acidified with 1N HCl and extracted with ethyl acetate (400+100 mL). The combined organic phases were dried (MgSO$_4$) to give 2.238 g of a light yellow powder.

Step 6: 2 M aqueous sodium carbonate (7.55 mL, 15.1 mmol) was added to a solution of the compound from step 3 (0.820 g, 2.00 mmol), the compound from 5 (0.883 g, 2.00 mmol) and [1,1'-bis(diphenylphosphino)ferrocene]dichloropalladium (II).methylene chloride (0.267 g, 0.327 mmol) in anhydrous DMF (10 mL). The reaction was warmed to 85° C. for 2.5 h. It was then cooled to RT, diluted with ethyl acetate (400 mL), and extracted with water (150 mL). The aqueous phase was washed with ethyl acetate (100 mL) and acidified with 1N HCl. The resulting slurry was extracted with ethyl acetate (400+100 mL), the combined organic phases were dried (MgSO$_4$) and concentrated in vacuo to give a white solid. The white solid was slurried with ether, filtered and air dried to give 0.932 g of product. Concentration in vacuo of the mother liquor produced another 0.359 g of desired product.

Step 7: S-(+)-1-(2-pyrrolidinylmethyl)pyrrolidine (0.200 mL, 1.23 mmol), HATU (0.434 g, 1.14 mmol) and diisopropylethyl amine (0.300 mL, 1.72 mmol) were added to a solution of the compound from step 6 (0.359 g, 0.557 mmol) in anhydrous DMF (3 mL) at RT. The reaction was stirred at RT for 3 h. The reaction was diluted with ethyl acetate (300 mL), washed with saturated aqueous sodium carbonate (50 mL×2), dried (MgSO$_4$) and concentrated in vacuo to give 0.675 g of an oil.

Step 8: TFA (4 mL) and water (0.100 mL) was added to a solution of the compound from step 7 (0.675 g) in acetonitrile (3.0 mL). After 4 h, the reaction was concentrated in vacuo and purified via reverse phase HPLC (acetonitrile/water) to give 0.123 g of product.

Example 4

Chemical Synthesis of Compound 10

Step 1: steps 1 and 2 of EXAMPLE 1 were carried out.

Step 2: S-(+)-1-(2-pyrrolidinylmethyl)pyrrolidine (5.3 g, 34.4 mmol), HATU (17.5 g, 46.0 mmol) and diisopropylethyl amine (17 mL, 97.6 mmol) were added to a solution of the compound from step 1 (8.50 g, 31.1 mmol) in anhydrous DMF (100 mL) at RT. The reaction was stirred at RT for 0.75 h. The reaction was diluted with ethyl acetate, washed with saturated aqueous sodium bicarbonate and water, dried (MgSO$_4$) and concentrated in vacuo to give 13 g of the desired product.

Step 3: The compound from step 2 (6.5 g, 15.8 mmol) was dissolved in 1:1 THF/saturated aqueous lithium hydroxide (50 mL) at RT. After 2 h, the reaction was concentrated in vacuo, acidified with saturated ammonium chloride and concentrated in vacuo. The resulting solid was slurried in THF and filtered. The filtrate was concentrated in vacuo to give the desired product.

Step 4: L-cyclohexylglycine tbutyl ester.HCl (3.75 g, 15.0 mmol), HATU (7.5 g, 19.7 mmol) and diisopropylethyl amine (10 mL, 57 mmol) were added to a solution of the compound from step 3 in anhydrous DMF (200 mL) at RT. The reaction was stirred at RT for 0.5 h. The reaction was diluted with ethyl acetate, washed with saturated sodium bicarbonate and water, dried (MgSO$_4$) and concentrated in vacuo to give the desired product.

Step 5: A solution of the compound from step 2 (6.5 g, 15.8 mmol), bis(pinacolate)diboran (4.4 g, 17.3 mmol), [1,1'-bis(diphenylphosphino)ferrocene]dichloropalladium (II).methylene chloride (0.388 g, 0.475 mmol) and potassium acetate (4.7 g, 47.9 mmol) in anhydrous DMF (100 mL) was warmed to 80° C. under a nitrogen atmosphere for 2 h. The reaction was then cooled to RT, diluted with ethyl acetate, washed with 5% citric acid and 5% sodium bicarbonate, dried (MgSO$_4$) and concentrated in vacuo to give a brown oil.

Step 6: 2 M aqueous sodium carbonate (40 mL, 80 mmol) was added to a solution of the compound from step 4, the compound from step 5 and [1,1'-bis(diphenylphosphino)-ferrocene]dichloropalladium (II).methylene chloride in anhydrous DMF (100 mL). The reaction was warmed to 80° C. overnight. It was then cooled to RT, acidified with saturated ammonium chloride and extracted with THF (10×). The combined organic phases were dried (MgSO$_4$) and concentrated in vacuo to give the carboxylic acid. One half of the material was used as crude material and half was purified via reverse phase HPLC (acetonitrile/water).

Step 7: Diethylcyanomethylphosphonate (2.7 mL, 16.7 mmol) was added dropwise to a slurry of NaH/mineral oil (0.730 g, 19.0 mmol) in anhydrous THF (10 mL) at RT. After the initial bubbling ceased, the reaction was warmed to reflux for 0.25 h. A solution of 3-nitrobenzophenone (1.90 g, 8.36 mmol) in anhydrous THF (20 mL) was added dropwise and the reaction warmed at reflux for 3 h. After cooling to RT, the reaction was poured into citric acid solution and extracted with ethyl acetate (2×). The combined organic phases were washed with water, dried (MgSO$_4$) and concentrated in vacuo. The residue was purified via flash column chromatography (methylene chloride) to give 1.81 g of an oil.

Step 8: A slurry of 10% Pd/C (0.500 g) and the compound from step 7 (1.81 g) in ethyl acetate (50 mL) was subjected to a hydrogen atmosphere (60 psi) at RT. After 18 h the reaction slurry was filtered and concentrated in vacuo to give 1.50 g of the desired product.

Step 9: 1M Borane tetrahydrofuran complex/THF (28 mL, 28 mmol) was added to a solution of the compound from step 8 (1.50 g) in anhydrous THF. The reaction was warmed to reflux for 3 days, cooled to RT and quenched with methanol. After the initial bubbling had ceased, more methanol (15 mL) was added and the reaction warmed to reflux for 0.5 h. The reaction was concentrated in vacuo, diluted with methanol, filtered and the filtrate concentrated in vacuo to give the desired product.

Step 10: The compound from step 9 (0.127 g, 0.561 mmol), HATU (0.110 g, 0.289 mmol) and diisopropylethyl amine (excess) were added to a solution of the compound from step 6 in anhydrous DMF (5 mL) at RT. The reaction was stirred at RT for 0.5 h. The reaction was diluted with ethyl acetate, washed with saturated sodium bicarbonate and water, dried (MgSO$_4$), concentrated in vacuo and purified via reverse phase HPLC to give 0.005 of the desired product.

Step 11: A solution of the compound from step 10 in 1:1 TFA/methylene chloride was stirred at RT for 2 h, concentrated in vacuo and purified via reverse phase HPLC to give 0.0015 g of the desired product.

Example 5

Chemical Synthesis of Compound 11

Step 1: 4-nitrodiphenylmethane (1.00 g, 4.69 mmol) was slowly added to a slurry of potassium t-butoxide (1.05 g, 9.36 mmol) in anhydrous DMF (20 mL) at RT. After 5 min. t-butyl bromoacetate (1.0 mL, 6.77 mmol) was added and the reaction stirred overnight at RT. The reaction was diluted with ether, washed with 5% citric acid solution and water, dried (MgSO$_4$) and concentrated in vacuo to give an oil. The oil was purified via flash column chromatography (60:40 methylene chloride/hexanes) to give a colorless solid.

Step 2: The compound from step 1 was dissolved in 1:1 TFA/methylene chloride (20 mL) at RT. After 0.5 h the reaction solution was concentrated in vacuo. The residue was dissolved in anhydrous methylene chloride, DMF (1 drop) and 2M oxalyl chloride/methylene chloride (10 mL, 20 mmol) was added. After 0.5 h bubbling ceased, and the reaction was concentrated in vacuo. The residue was dissolved in toluene (25 mL) and ammonia gas was bubbled into the reaction for 0.5 h. The reaction was diluted with ethyl acetate, washed with sodium bicarbonate solution, dried (MgSO$_4$) and concentrated in vacuo to give 0.560 g of a colorless oil.

Step 3: 1M Borane tetrahydrofuran complex/THF (10 mL, 10 mmol) was added to a solution of the compound from step 2 (0.560 g) in anhydrous THF (10 mL). The reaction was warmed to reflux overnight, cooled to RT and quenched with methanol. After the initial bubbling had ceased, more methanol (10 mL) was added and the reaction warmed to reflux for 0.5 h. The reaction was concentrated in vacuo, and purified via flash column chromatography (80:20:2 ethyl acetate/methanol/triethylamine) to give 0.130 g of a light yellow oil.

Step 4: Diisopropylethylamine (0.200 mL, 1.12 mmol) was added to a solution of the compound from step 3 (0.130 g, 0.507 mmol), the compound from Example 4, step 6 (0.250 g, 0.313 mml) and HATU (0.200, 0.526 mmol) in anhydrous DMF (10 mL) at RT. After 0.5 h the reaction was concentrated in vacuo, dissolved in ethyl acetate, washed with saturated sodium bicarbonate and water, dried (MgSO$_4$), concentrated in vacuo and purified via reverse phase HPLC (acetonitrile/water) to give 0.140 g of an off-white powder.

Step 5: A solution of the compound from step 4 (0.010 g) in 1:1 TFA/methylene chloride (4 mL) was stirred at RT for 2 h. The reaction was then concentrated in vacuo and purified via reverse phase HPLC (acetonitrile/water) to give a white solid.

Example 6

Chemical Synthesis of Compound 9

Step 1: 2M (trimethylsilyl)diazomethane/hexanes (0.100 mL, 0.200 mmol) was added to a solution of the compound from Example 3, step 8 (0.020 g, 0.023 mmol) in acetonitrile (0.5 mL). The reaction was stirred at RT for 0.25 h, concentrated in vacuo and purified via reverse phase HPLC (acetonitrile/water) to give a white solid.

Example 7

Binding Assay to Assess Whether a Compound Binds CD154 and Inhibits CD40:CD154 Interaction 1) Ninety-six well plates of Nunc Maxisorp were coated with 100 µl of 5–10 µg/ml human CD40-Ig produced in Pichia cells, (in PBS pH 7.2) per well, covered with plate sealers (Costar, Cat. No. 3095) and stored overnight at 4° C.

2) The CD40-Ig-coated plates were shook out and blotted dry.

3) The CD40-Ig-coated plates were blocked with 300 µl per well of PBS (0.05% Tween-20, 1% BSA, pH 7.2) at RT for one hour or in the refrigerator for up to 3 weeks.

4) The CD40-Ig-coated plates were washed 3× with PBS+0.05% Tween-20 pH 7.4 with plate washer at RT.

5) The plates were optionally blotted dry.

6) Primary Screening of compounds:
a. Compounds were titrated in 100 mM Hepes+0.005% BSA pH 7.2 in Titertube (Bio-Rad Laboratories) and 50 µl of titrated compounds was then added into each well of the plate.

IC50 parameters:
One 7 point curve per compound was generated where each point was run in triplicate. A 2× dilution series was used to generate the curve.
Top concentration in assay of test compound was 125 µM.

b. Fifty µl/well of 0.07–1.6 µg/ml biotin-CD154 in 100 mM Hepes+0.005% BSA (pH 7.2) was added per well. Final concentration of biotin-CD154 was 0.035–0.08 µg/ml. It was mixed with compound in each well in the plate.

c. The plates were covered with plate sealer and incubated for one-hour at RT.

7) The plates were washed 3× with plate washer with PBS+0.05% Tween-20 (pH 7.4) at RT.

8) The plates were optionally blotted dry.

9) 100 µl of a 1/300,000 dilution of HRP-Strep/Avidin (Jackson Immuno Research Code3 #016-030-084) was added to each well. Dilution buffer was: PBS+0.05% Tween-20. The plates were covered with plate sealer and incubated for one hour at room temperature.

10) The plates were washed with plate washer 3× at RT.

11) The plates were optionally blotted dry.

12) 100 µl/well of TMB(1-component) (Kirkegarrd & Perry Labs, Prod #50-76-04) was added to each well and incubated at RT about 10 min.

13) 100 µl/well of 0.18M H$_2$SO$_4$ was added to stop reaction in the plates.

14) The plates were read within 30 minutes of stopping the reaction at 450 nM on a microplate reader (Molecular Devices Co.).

Compounds that bound to CD154 and blocked CD40:CD154 interaction prevented CD154 from binding to immobilized CD40-Ig and gave a low absorbance reading.

Controls:
1. Total reaction: Reaction well contained 50 µl of 100 mM Hepes/0.005% BSA (no test compound)
2. Positive control: Reaction well contained 10 µl of 1 mg/ml 5c8(anti-CD154 mAb) and 50 µl of 100 mM Hepes/0.005% BSA.
3. Blank control: Reaction well contained 100 µl 100 mM Hepes/0.005% BSA.
4. Compound control: Titration series in triplicate of BIO-002108-00.

BIO-002108-00 is one of the derivatives of suramin (CalBiochem catalog number 574625). It has been demonstrated that BIO-002108-00, as well as other derivatives of suramin, is a CD40:CD154 binding interrupter. BIO-002108-00 has an IC50 in the A range (less than 50 µM) for CD40:CD154 binding interruption as determined by this assay. BIO-002108-00 has an IC50 of greater than 125 µM (average value) for TNF-α:TNFRp60 binding interruption. BIO-002108-00 has the following structure:

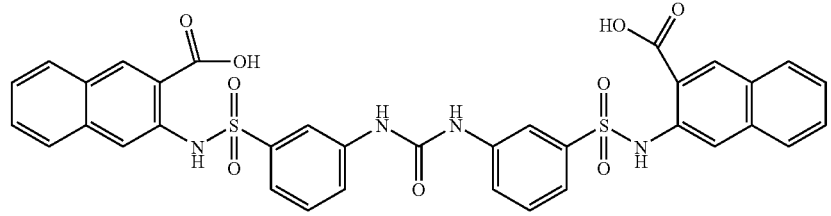

BIO-002108-00

It was synthesized by the following method:

Step 1

2M (Trimethylsilyl)diazomethane/hexanes (50 mL, 100 mmol) was added dropwise to a solution of tech. 3-amino-2-naphthoic acid (3 g, 12.8 mmol) in methanol (300 mL) at RT. A grey precipitate was formed. The reaction was centrifuged, the supernatant was decanted, concentrated in vacuo and purified via flash column chromatography (methylene chloride) to give 1.78 g of a yellow crystalline solid.

Step 2

A solution of the compound from step 1 (0.205 g, 1.02 mmol) and 3-nitrobenzenesulfonyl chloride (0.250 g, 1.13 mmol) in pyridine (5 mL) was stirred at RT for 0.5 h. The reaction was then poured into 1N aqueous hydrochloric acid (100 mL) and extracted with methylene chloride (2×100 mL). The combined organic phases were washed with 1N aqueous hydrochloric acid (100 mL) and water (100 mL), dried ($MgSO_4$) and concentrated in vacuo to give 0.380 g of a reddish syrup.

Step 3

10% Pd/C (0.500 g) was added to a solution of the compound from step 2 (0.380 g) in 1:1 ethyl acetate/methanol (50 mL). The reaction was stirred under a hydrogen atmosphere (1 atm) for 16 h. The reaction was centrifuged, the supernatant decanted, concentrated in vacuo and purified via flash column chromatography (95:5 methylene chloride/ethyl acetate) to give 0.278 g of a white solid.

Step 4

A solution of the compound from step 3 (0.060 g, 0.169 mmol) and 1,1'-carbonyldiimidazole (0.030 g, 0.185 mmol) in anhydrous THF (1 mL) was refluxed overnight. The reaction was then cooled to RT, concentrated in vacuo and purified via reverse phase HPLC (acetonitrile/water) to give 0.018 g of a white solid.

Step 5

Lithium hydroxide (0.100 g, 2.28 mmol) was added to a solution of the compound from step 4 (0.018 g) in 2:1:1 THF/methanol/water (20 mL). After stirring overnight at RT, the reaction was poured into 1N aqueous hydrochloric acid (25 mL) and extracted with ethyl acetate (2×50 mL). The combined organic phases were dried ($MgSO_4$) and purified via reverse phase HPLC (acetonitrile/water) to give 0.001 g white solid.

MS (ESP−) 709.09 (M−1)

Example 8

Binding Assay to Assess Whether A Compound Binds to TNF-α and Inhibits TNF-α/TNFRp60 Interaction 1) Ninety-six well plates of Nunc Maxisorp were coated with 100 μl/well of 0.6 ug/ml tumor necrosis factor receptor p60 (TNFRp60) (Browning, J. L.; Douglas, I.; Ngam-ek, A.; Bourdon, P. R.; Ehrenfels, B. N.; Miatkowski, K.; Zafari, M.; Yampaglia, A. M.; Lawton, P.; Meier, W.; Benjamin, C. P.; Hession, C. *J. Immunol.* 1995, 154, 33–46) in PBS, pH 7.2, covered with plate sealers (Costar, Cat. No. 3095) and stored overnight at 4° C.

2) The coated plates were shook out and blotted dry.

3) TNFRp60-coated plates were blocked with 300 μl per well of PBS (0.05% Tween-20, 1% BSA, made from media prep) at 4° C. for one hour. Plates were stored for 3 weeks at 4° C.

4) The plates were washed 3× with PBS+0.05% Tween-20) by plate washer at room temperature.

5) The plates were optionally blotted dry.

6) Primary Screening of compounds

Compounds were titrated in 100 mM Hepes+0.005% BSA, pH 7.2 in Titertube (Bio-Rad Laboratories) and then 50 μl of titrated compounds was added into each well of the plate.

IC50 parameters: One 7 point curve per compound was generated where each point was run in triplicate. A 2× dilution series was used to generate the curve. The top concentration in assay of test compound was 125 μM.

50 μl/well of 8 ng/ml Biotin-TNF-α (R&D System) in 100 mM Hepes+0.005% BSA, pH 7.2 were added. The final concentration of Biotin-TNFα was 4 ng/ml. It was mixed with compound in each well in the plate. The plates were covered with sealer and incubated one hour at RT.

7) The plates were washed 3× by plate washer with PBS+0.05% Tween-20 at RT.

8) The plates were optionally blotted dry.

9) 100 μl of Streptavidin-HRP (diluted at 1:300,000 in PBS+0.05% Tween-20) was added to each well. The plates were covered with sealer and incubated one hour at RT.

10) The plates were washed by plate washer 3× at RT.

11) The plates were optionally blotted dry.

12) 100 μl/well of TMB(1-component)(Kirkegarrd & Perry Labs, Prod #50–76–04) were added at RT and incubated about 10 min in dark environment.

13) 100 μl/well of 0.18M $H_2SO_4$ was added to stop the reaction.

14) The plates were read within 30 minutes of adding stop reagent at 450 nM by microplate reader (Molecular Devices Co.)

Controls:

Total reaction: Reaction well contained 50 μl of 100 mM Hepes/0.005% BSA (no test compound).

Positive control: Reaction well contained 10 μl of 1.5 mg/ml anti-TNF-α and 50 ul of 100 mM Hepes/0.005% BSA.

Blank control: Reaction well contains 100 μl 100 mM Hepes/0.005% BSA.

Compound control: Titration series in triplicate of BIO-002108-00.

Compounds that blocked TNF-α/TNFRp60 interaction prevented TNF-α from binding to immobilized TNFRp60 and gave a low absorbance reading.

The above-described assay may also be carried out using TNFRp60-Fc in place of TNFRp60.

In addition to the foregoing assays (Examples 7–8), the following binding assay may be used to assess activity of compound according to this invention.

Example 9

ICAM Assay

1. Set up wells containing:
   Different concentrations of compounds in 50 uL of RPMI (10% serum, 4 mM glutamine, pen/strep)
   0.5 ug of CD40 ligand in 50 uL
   $2×10^5$ 2G6 cells in 100 uL
   Set up groups of cells only
   Cells+compound
   Cells+ligand
   Cells+ligand+10 ug of 5c8 mAb
   Each group should have a final volume in the well of 200 uL. If the concentration of DMSO >0.22%, there should be that control+ligand.

b. Incubate the plates at 37° C. for 18 hours in a $CO_2$ incubator.

c. Add 40 uL of lysis buffer (part of sICAM-1 kit from Endogen EH-5400) to the wells and pipet up and down.

d. Shake for ½ hour on rocker platform RT at 150 RPMs/min.

e. Make a 1:1 dilution (40 uL of lysate+40 uL of diluent from sICAM-1 kit from Endogen EH-5400) in Falcon microtest flexible assay plates.
f. Pipet 25 uL of this mixture into ELISA kit plate (sICAM-1 precoated plate, Endogen) Also, pipet 25 uL of standards on the plate.
g. Add 75 uL of HRP-conjugated Anti-ICAM-1 antibody (from sICAM-1 kit from Endogen EH-5400) to all wells except the blank.
h. Cover the plate and incubate 2 hrs at RT on shaking platform 150 RPM/min.
i. Wash plate using T-Cell protocol on plate washer. The wash buffer is PBS+0.05% tween-20.
j. Dissolve 1 tablet of OPD per 5 mL of substrate buffer (from sICAM-1 kit from Endogen EH-5400, use 15 mL/plate).
k. Pipet 100 uL into each well.
l. Incubate uncovered for 30 minutes at RT.
m. Add 50 uL of 2N $H_2SO_4$ to stop the reaction.
n. Read absorbance at 490 nM.
Positive control: Cells Plus ligand
Negative control: Cells only, no ligand
Experimental control: Cells plus ligand plus 10 ug of 5c8 mAb.

EQUIVALENTS

The invention may be embodied in other specific forms without departing from the spirit or essential characteristics thereof. The foregoing embodiments are therefore to be considered in all respects illustrative of, rather than limiting on, the invention disclosed herein. All changes which come within the meaning and range of equivalency of the claims are intended to be embraced therein.

We claim:

1. A compound, which interrupts CD40:CD154 interaction, of the formula:

Formula II

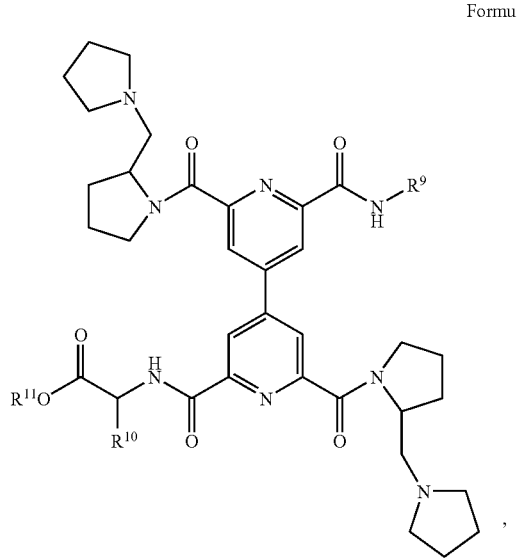

wherein,

R$^9$ is selected from the group consisting of C1–5 alkyl-aryl, cycloalkyl and alkenylaryl; wherein the alkyl is optionally substituted with aryl and the aryl is optionally substituted with one to four halogens, aryl, $NH_2$ or $NO_2$;

R$^{10}$ is selected from the group consisting of alkyl and cycloalkyl; and

R$^{11}$ is selected from the group consisting of H and alkyl.

2. A compound, which interrupts CD40:CD154 interaction, of the formula:

Formula III

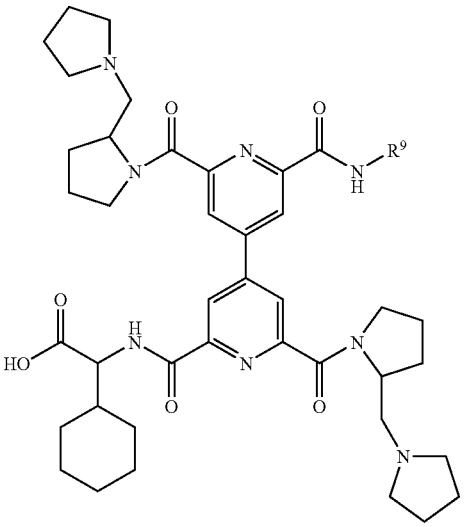

wherein,

R$^9$ is selected from the group consisting of C1–5 alkyl-aryl;

wherein alkyl and aryl are optionally substituted with aryl.

3. A compound, which interrupts CD40:CD154 interaction, wherein said compound is selected from the group consisting of:

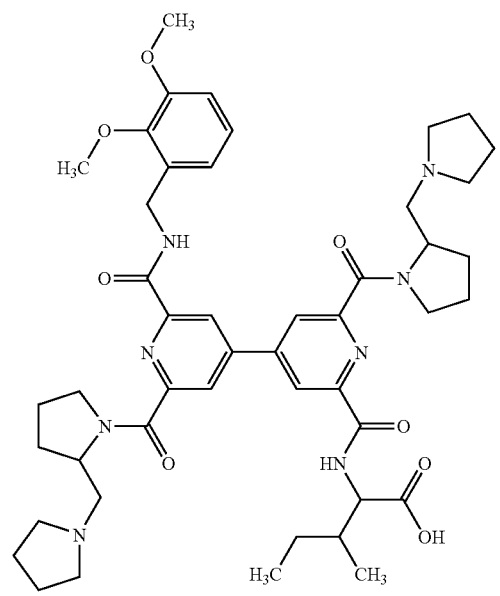

-continued
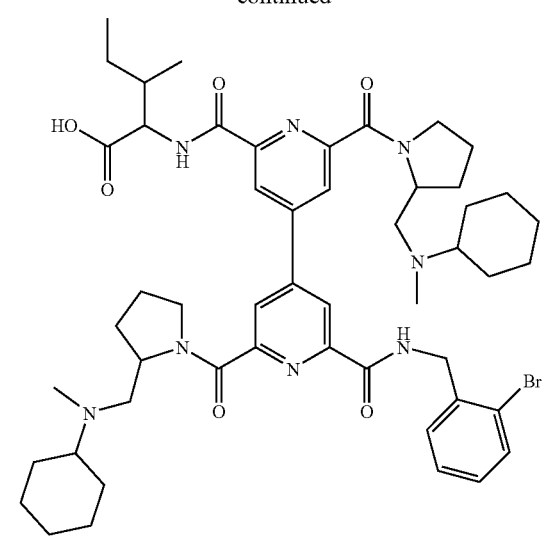
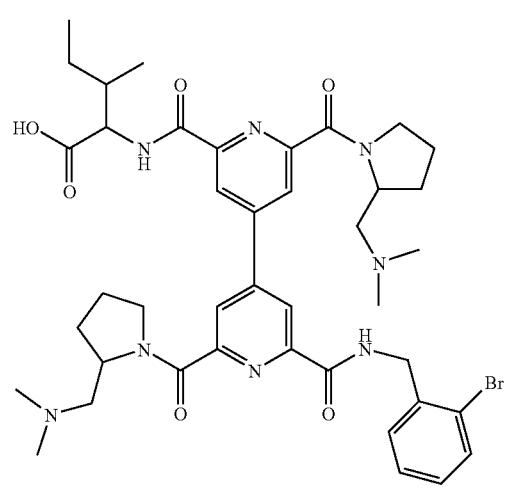
and
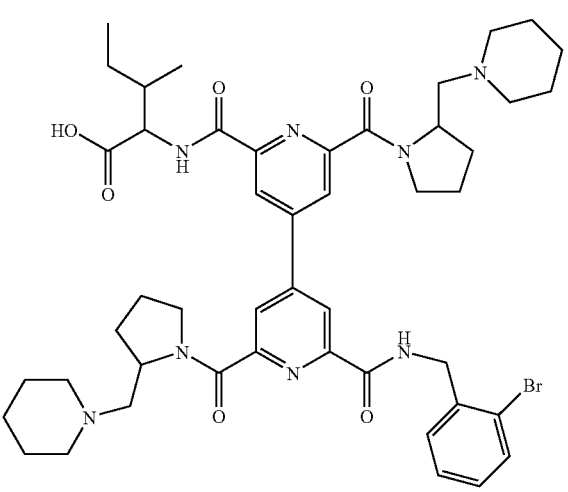
4. A compound, which interrupts CD40:CD154 interaction, wherein said compound is selected from the group consisting of:
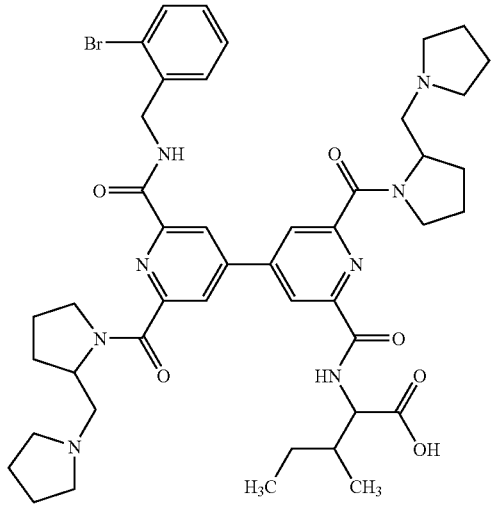
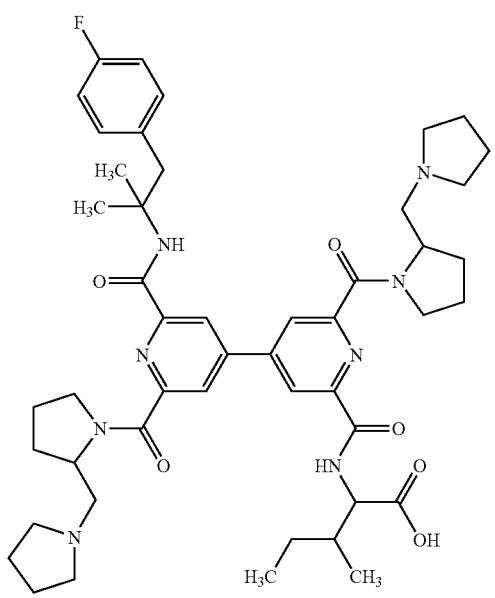
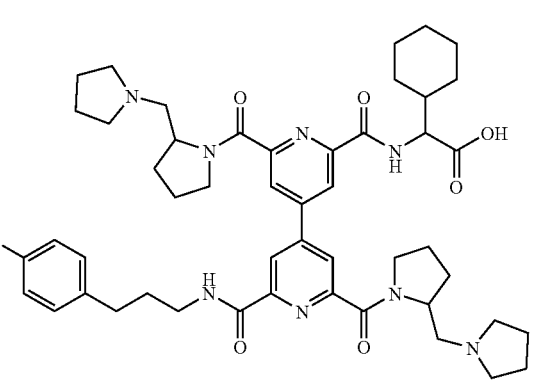

-continued
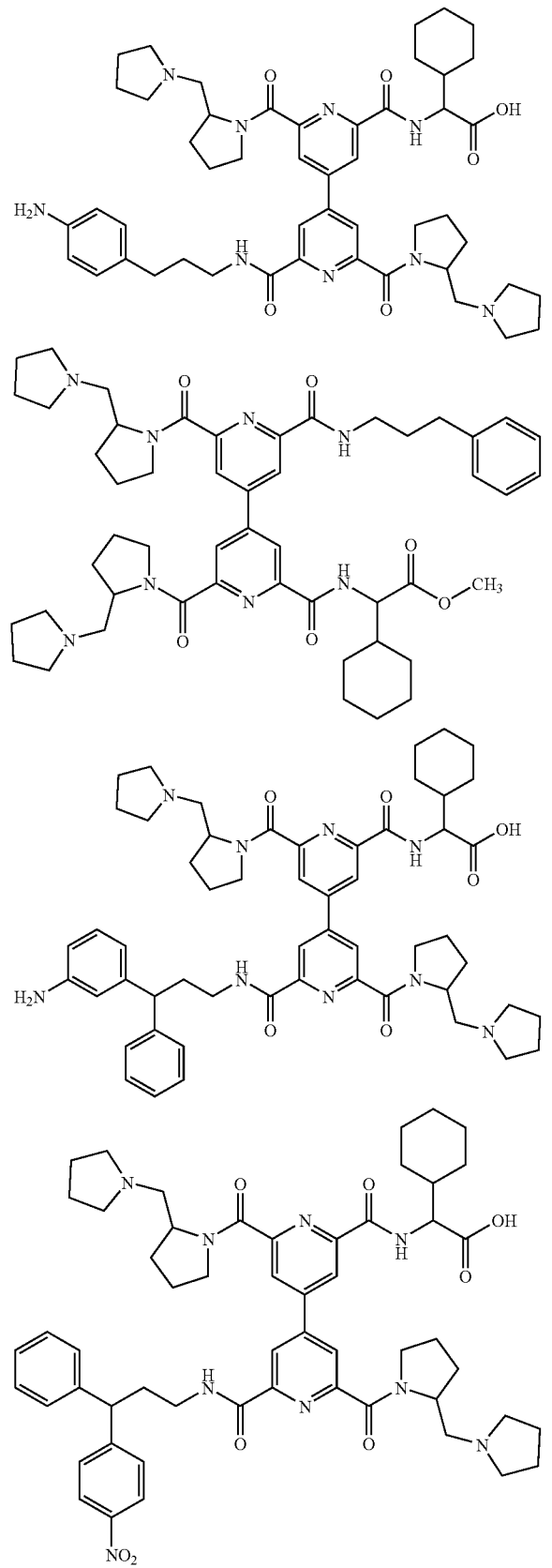
-continued
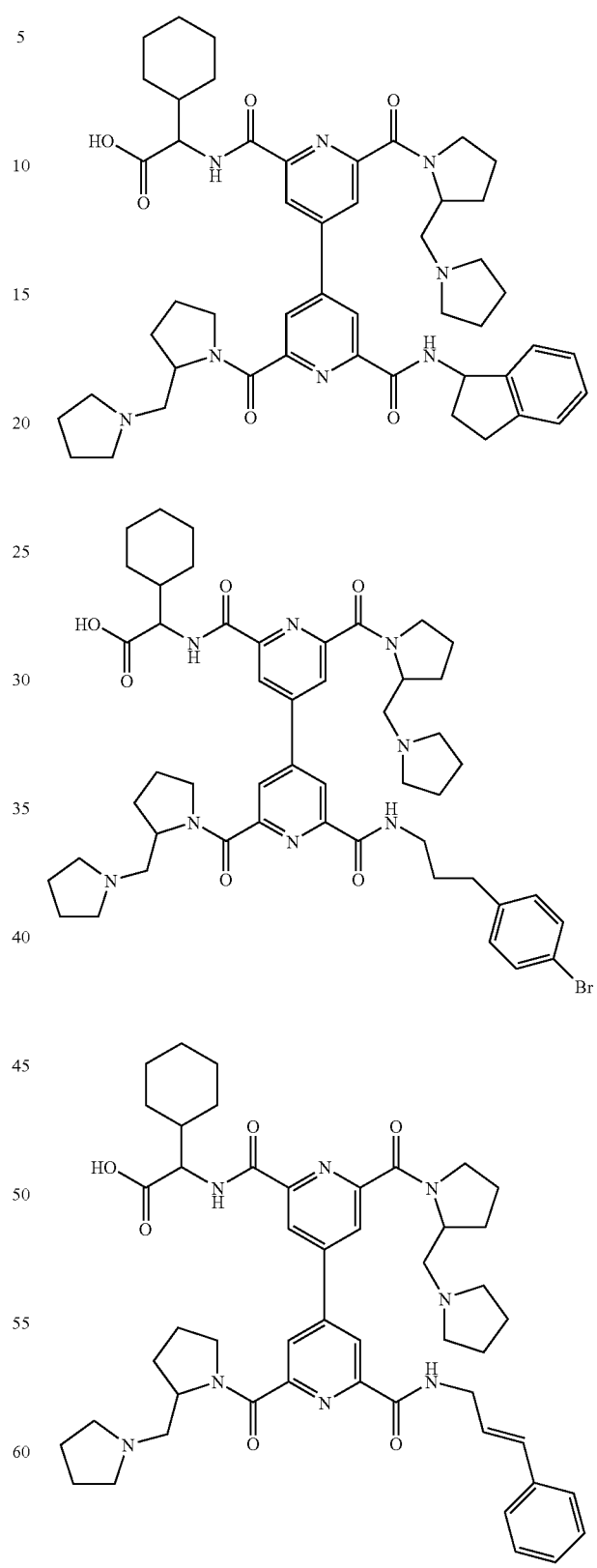

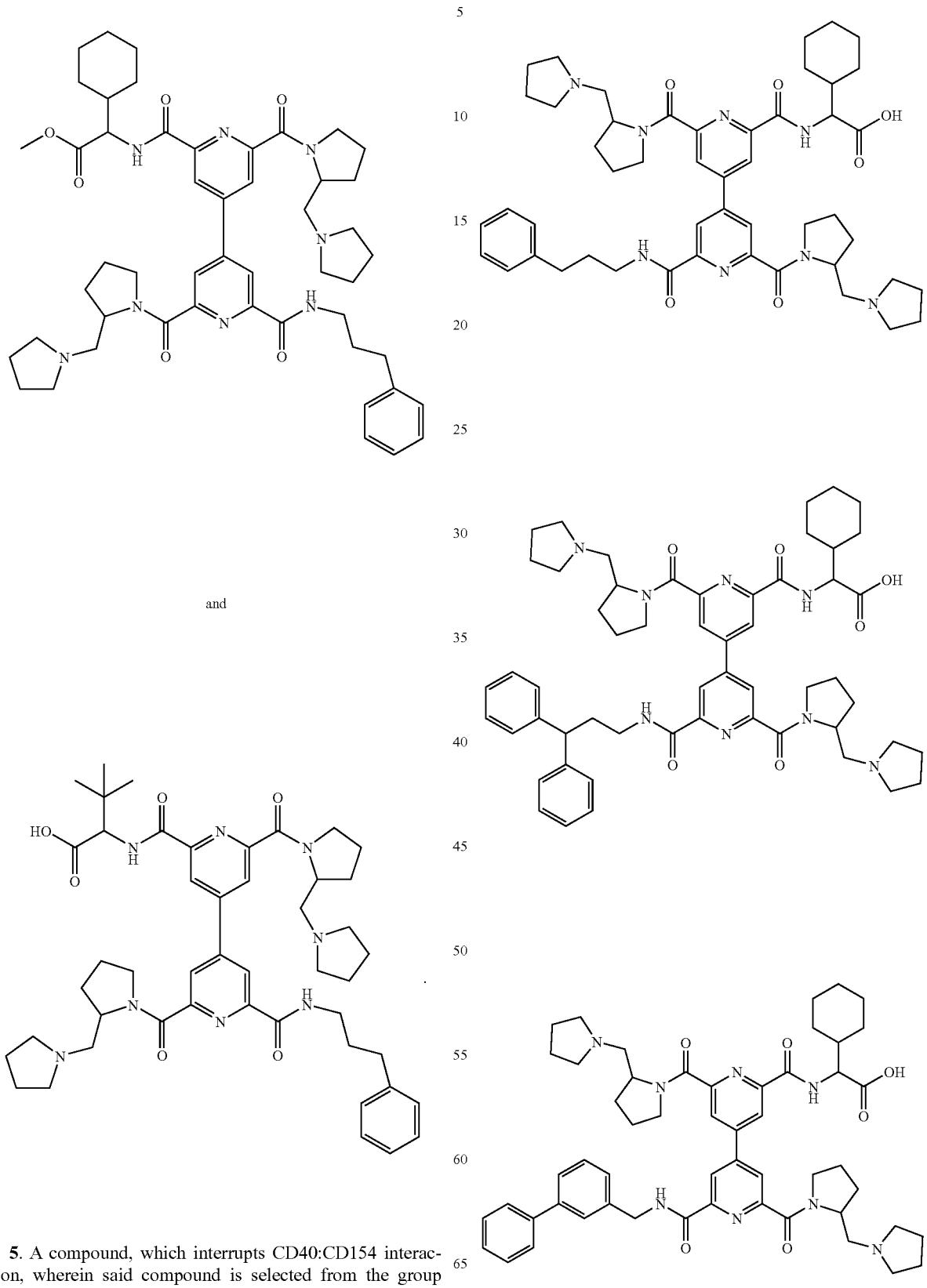
5. A compound, which interrupts CD40:CD154 interaction, wherein said compound is selected from the group consisting of:

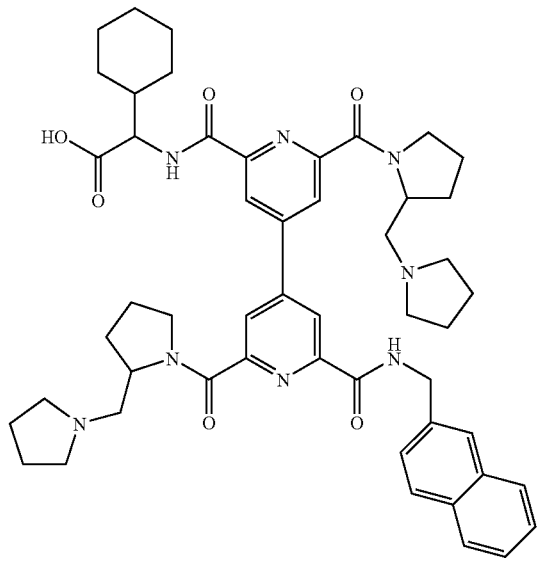
and
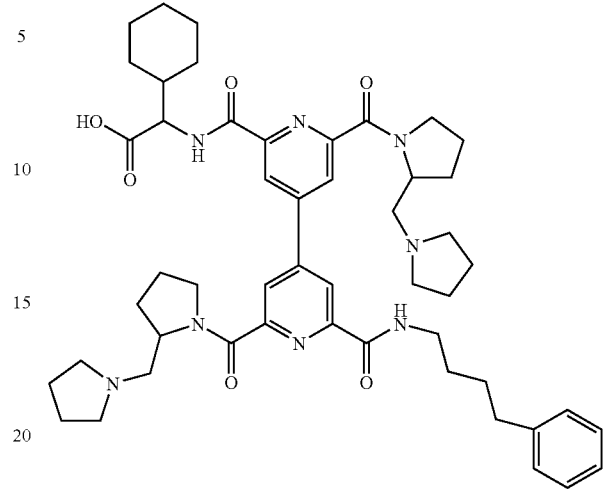
6. A pharmaceutical composition comprising a pharmaceutically acceptable carrier and a compound according to any one of claims 1–5.
* * * * *